(12) United States Patent
Jamieson et al.

(10) Patent No.: US 7,514,229 B2
(45) Date of Patent: Apr. 7, 2009

(54) METHODS FOR DIAGNOSING AND EVALUATING TREATMENT OF BLOOD DISORDERS

(75) Inventors: Catriona Helen M. Jamieson, Palo Alto, CA (US); Irving L. Weissman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 90 days.

(21) Appl. No.: 11/528,890

(22) Filed: Sep. 27, 2006

(65) Prior Publication Data

US 2007/0111238 A1    May 17, 2007

Related U.S. Application Data

(60) Provisional application No. 60/722,371, filed on Sep. 29, 2005.

(51) Int. Cl.
*G01N 33/53* (2006.01)
*C12N 5/00* (2006.01)
*C12N 5/02* (2006.01)

(52) U.S. Cl. .................. 435/7.21; 435/373; 435/375

(58) Field of Classification Search ................. None
See application file for complete search history.

(56) References Cited

U.S. PATENT DOCUMENTS 6,465,247 B1    10/2002    Weissman et al.

FOREIGN PATENT DOCUMENTS

WO    WO 99/10478    3/1999

OTHER PUBLICATIONS

Sutherland et al., Blood, 1996, V.87, pp. 4754-4761.*
Akashi, K., et al., "A clonogenic common myeloid progenitor that gives rise to all myeloid lineages," (2000) *Nature*, 404:193-197.
Baxter, E., et al., "Acquired mutation of the tyrosine kinase JAK2 in human myeloproliferative disorders," (2005) *The Lancet*, 365:1054-1061.
Demeure, C., et al., "CD47 Engagement inhibits cytokine production and maturation of human dendritic cells," (2000) *The Journal of Immunology*, 164:2193-2199.
James, C., et al., "A unique clonal *JAK2* mutation leading to constitutive signaling causes polycythaemia vera," (2005) *Nature*, 434:1144-1148.
Jamieson, C., et al., "Chronic versus acute myelogenous leukemia: A question of self-renewal," (2004) *Cancer Cell*, 531-533.
Jamieson, C., et al., "Granulocyte-macrophage progenitors as candidate leukemic stem cells in blast-crisis CML," (2004) *New England Journal of Medicine*, 351(7):657-667.
Kravolics, R., et al., "A gain-of-function mutation of JAK2 in myeloproliferative disorders," (2005) *New England Journal of Medicine*, 352(17):1779-1790.
Levine, R., et al., "Activating mutation in the tyrosine kinase JAK2 in polycythemia vera, essential thrombocythemia, and myeloid metaplasia with myelofibrosis," (2005) *Cancer Cell*, 7:387-397.
Passegueé, E., et al., "JunB deficiency leads to a myeloproliferative disorder arising from hematopoietic stem cells," (2004) *Cell*, 119:431-443.

* cited by examiner

*Primary Examiner*—Michail A Belyavskyi
(74) *Attorney, Agent, or Firm*—Bozicevic, Field & Francis LLP; Pamela J. Sherwood

(57) ABSTRACT

Methods, systems and kits are provided for the clinical staging of blood disorders including myelodysplastic syndrome, myeloproliferative diseases and leukemias by differential analysis of hematologic samples for the distribution of one or more hematopoietic stem or progenitor cell subsets. Additional functional, genetic, gene expression, proteomic or other molecular analyses of the hematopoietic stem and progenitor cells from the patients can also be employed in the staging methods of the invention.

8 Claims, 10 Drawing Sheets

SEQUENCE LISTING

<160> NUMBER OF SEQ ID NOS: 8

<210> SEQ ID NO 1
<211> LENGTH: 21
<212> TYPE: DNA
<213> ORGANISM: human

<400> SEQUENCE: 1
acaacagtca aacaacaatt c                                              21

<210> SEQ ID NO 2
<211> LENGTH: 17
<212> TYPE: DNA
<213> ORGANISM: human

<400> SEQUENCE: 2
acacctagct gtgatcc                                                   17

<210> SEQ ID NO 3
<211> LENGTH: 21
<212> TYPE: DNA
<213> ORGANISM: human

<400> SEQUENCE: 3
cgtctccaca gacacatact c                                              21

<210> SEQ ID NO 4
<211> LENGTH: 35
<212> TYPE: DNA
<213> ORGANISM: human

<400> SEQUENCE: 4
aaaggcatta gaaagcctgt agttttactt actct                               35

<210> SEQ ID NO 5
<211> LENGTH: 29
<212> TYPE: DNA
<213> ORGANISM: human

<400> SEQUENCE: 5
taaaggcgta cgaagagaag taggagact                                      29

<210> SEQ ID NO 6
<211> LENGTH: 21
<212> TYPE: DNA
<213> ORGANISM: human

<400> SEQUENCE: 6
ggcccatgcc aactgtttag c                                              21

<210> SEQ ID NO 7
<211> LENGTH: 20
<212> TYPE: DNA
<213> ORGANISM: human

<400> SEQUENCE: 7
acggtcaact gcatgaaaca                                                20

<210> SEQ ID NO 8
<211> LENGTH: 21
<212> TYPE: DNA
<213> ORGANISM: human

-continued

<400> SEQUENCE: 8
gttgctaaac agttggcatg g                    21

METHODS FOR DIAGNOSING AND EVALUATING TREATMENT OF BLOOD DISORDERS

This invention was made with Government support under contracts CA086065 and CA086017 awarded by the National Institutes of Health. The Government has certain rights in this invention.

Blood disorders can be categorized into a number of different types. Among these are the myeloproliferative disorders, myelodysplastic syndromes, and leukemias. In general, blood disorders involve the distorted proliferation and development of white blood cells in bone marrow and blood.

Myeloproliferative disorders (MPDs) are a group of disorders characterized by abnormal proliferation of one or more hematopoietic cell lines or connective tissue elements. The myeloproliferative disorders include polycythemia vera (PV), myelofibrosis, chronic myelogenous (myelocytic) leukemia (CML), and essential thrombocythemia (ET). Some hematologists also include acute leukemia, especially erythroleukemia, and paroxysmal nocturnal hemoglobinuria among the myeloproliferative disorders.

Clinical and laboratory features of leukemia are caused by suppression of normal blood cell formation and organ infiltration. Inhibitory factors produced by leukemic cells or replacement of marrow space may suppress normal hematopoiesis, with ensuing anemia, thrombocytopenia, and granulocytQpenia. Organ infiltration results in enlargement of the liver, spleen, and lymph nodes, with occasional kidney and gonadal involvement. Meningeal infiltration results in clinical features associated with increasing intracranial pressure (e.g., cranial nerve palsies).

Leukemias were originally termed acute or chronic based on life expectancy but now are classified according to cellular maturity. Acute leukemias consist of predominantly immature cells (usually blast forms); chronic leukemias, more mature cells. Acute leukemias are divided into lymphoblastic (ALL) and myelogenous (AML) types. Chronic leukemias are described as lymphocytic (CLL) or myelocytic (CML).

Myelodysplastic syndromes represent progressive bone marrow failure but with an insufficient proportion of blast cells (<30%) for definite diagnosis of AML; 40 to 60% of cases evolve into AML.

Present techniques for diagnosing blood disorders and for evaluating effectiveness of treatment are time consuming and rarely, if ever, provide an unambiguous results. Therefore, it is of considerable interest to develop a quick, accurate and positive diagnostic and evaluation procedure that is capable of accurately staging blood disorders. The present invention satisfies these, and other, needs.

SUMMARY OF THE INVENTION

Methods are provided for the clinical staging of human blood disorders, including myeloproliferative disorder (MPDs), leukemia, and myelodysplastic syndrome. Staging is useful for diagnosing blood disorders and prognosis as well as for evaluating the effectiveness of treatment. In the methods of the invention, a hematologic sample, e.g. blood, lymph, bone marrow aspirate, etc. is differentially analyzed for the presence of one or more hematopoietic stem or progenitor cells, which may include hematopoietic stem cells; myeloid progenitors; common lymphoid progenitors; megakaryocyte progenitors; etc., wherein the distribution of progenitor cells in the CD34$^+$ compartment of the blood is diagnostic of the stage and type of blood disorder.

In one embodiment of the invention, a blood sample from a subject with a blood disorder is stained with reagents specific for CD34; CD38; optionally a lineage panel; and one or more markers of CD90 (thy-1); flk-2; IL-3Rα; CD45RA; IL-7R; CD47. The analysis of staining patterns in the CD34$^+$ subset of blood cells provides the relative distribution of progenitor cells, which distribution predicts the stage and type of blood disorder.

In one embodiment of the invention, a patient sample is stained with a cocktail of reagents comprising binding partners specific for CD34, CD38, IL-3α, and CD45RA, where the distribution of hematopoietic stem cells (CD34$^+$CD38$^-$); common myeloid progenitor cells (CD34$^+$CD38$^+$CD45RA$^-$ IL-3Rα$^{lo}$); or myelomonocytic lineage progenitors (CD34$^+$ CD38$^+$CD45RA$^+$IL-3Rα$^{lo}$), and erythroid/megakaryocytic lineage progenitor (CD34$^+$CD38$^+$CD45RA$^-$IL-3Rα$^-$) distinguishes MPD in the patient.

In one embodiment, the patient sample is compared to a control, or a standard test value. In another embodiment, the patient sample is compared to a pre-leukemic sample, or to one or more time points through the course of the disease.

To augment this phenotypic analysis of blood disorders, certain embodiments of the invention include genetic and/or molecular analysis of the different hematopoietic stem and progenitor cell populations. Genetic analyses include identification of specific chromosomal abnormalities, genomic sequence variations, etc. Molecular analyses include gene expression profiles (e.g., mRNA expression patterns), protein expression analysis, signal transduction pathway analysis (e.g., analysis of kinase activity of a kinase of interest), etc.

In certain embodiments of the invention, transcription factor expression profiles are analyzed from hematopoietic stem and progenitor cell subsets, including but not limited to Pu.1, GATA-1, GATA-2, Jun, CEBP-α, and family members thereof. In other embodiments, a gene expression profile is obtained using microarray technology. Comparison of the gene expression profile of a sample to control samples (e.g., normal or previously diagnosed samples) aid in analysis.

In addition, certain embodiments of the invention include analyzing the growth potential of the hematopoietic stem and progenitor cells in defined culture conditions in vitro to aid in the diagnosis of MPDs and/or evaluation of therapeutic effectiveness.

DETAILED DESCRIPTION OF THE EMBODIMENTS

Figure 1A:
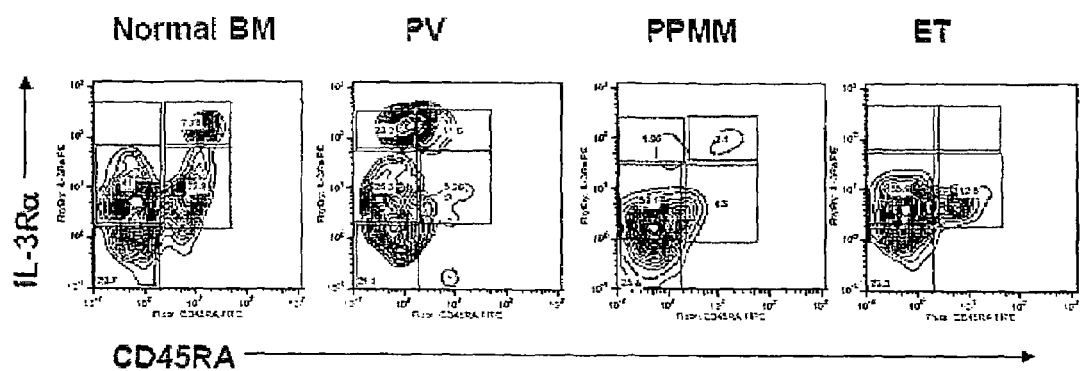
FIG. 1A. Phenotypic Stem and Progenitor Profiles of Normal versus MPD Samples FACS plots demonstrate decreased GMP in MPD with skewed erythroid or megakaryocytic differentiation potential including polycythemia vera (PV), post-polycythemic myelofibrosis with myeloid metaplasia (PPMM), and ET compared with normal bone marrow. In addition, PV progenitor profiles were typified by a previously uncharacterized CD34+ CD38+Lin– IL-3 receptor α++ CD45RA– population.

As summarized above, the subject invention is drawn to methods for the clinical staging of human blood disorders, including myeloproliferative disorders (MPDs), leukemias, and myelodysplastic syndrome. Staging is useful for diagnosing blood disorders and prognosis as well as for evaluating the effectiveness of treatment. The blood disorders of interest include, but are not limited to, polycythemia vera (PV), agnogenic myeloid metaplasia with myelofibrosis (AMM), chronic myelogenous (myelocytic) leukemia (CML), essential thrombocythemia (ET), Chronic Myelomonocytic Leukemias (CMML), Chronic leukocytic leukemia (CLL), acute lymphoblastic leukemia (ALL), acute myelogenous leukemia (AML), etc.

These blood disorders are staged by analysis of the presence of hematopoietic stem and/or progenitor cells, particularly progenitor cells dedicated to the myeloid lineage, which progenitor cells may include, but are not limited to, CMP (common myeloid progenitors); megakaryocyte erythroid progenitors (MEP), and myelomonocytic lineages (GMP).

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analyses (e.g., mutational analysis or gene expression profiling), proteomics, cell surface staining, or other means, in order to determine the presence of markers that are useful in classification. For example, genetic abnormalities can be causative of disease susceptibility or drug responsiveness, or can be linked to such phenotypes.

Hematopoietic Stem and Progenitor Cells

In general, samples containing white blood cells, particularly including blood or bone marrow samples, are stained with reagents specific for markers present of hematopoietic stem and progenitor cells, which markers are sufficient to distinguish the major stem and progenitor groups. The reagents, e.g. antibodies, may be detectably labeled, or may be indirectly labeled in the staining procedure. The data provided herein demonstrate that the number and distribution of progenitor cells is diagnostic of the stage of the leukemia.

Any combination of markers may be used that are sufficient to distinguish the stem/progenitor cells of interest. A marker combination of interest may include CD34 and CD38, which distinguishes hematopoietic stem cells (HSC), (CD34$^+$, CD38$^-$) from progenitor cells, which are CD34$^+$, CD38$^+$). The inclusion of CD45RA and IL-3Rα is also of interest because it allows a distinction between the three known myeloid progenitor cell subsets. In other embodiments, CD90 may be included. CD47 and Flk2 are found to be indicative of CMML. Lineage panels may be included to distinguish progenitor cells from lineage committed cells.

Bone marrow HSCs are functionally defined by their unique capacity to self-renew and to differentiate to produce all mature blood cell types. In general, the process of development from pluripotent progenitors to mature cells with specific functions involves the progressive loss of developmental potential to other lineages. A hierarchy has emerged in which each successive developmental stage loses the potential to become a specific cell type or class of cells. This stepwise developmental process has been considered linear in the sense that once a cell has made a developmental choice it cannot revert. The earliest known lymphoid-restricted cell in adult mouse bone marrow is the common lymphocyte progenitor (CLP), and the earliest known myeloid-restricted cell is the common myeloid progenitor (CMP). Importantly, these cell populations possess an extremely high level of lineage fidelity in in vitro and in vivo developmental assays. A complete description of these cell subsets may be found in Akashi et al. (2000) Nature 404(6774):193, U.S. Pat. No. 6,465,247; and published application U.S. Ser. No. 09/956,279 (common myeloid progenitor); Kondo et al. (1997) Cell 91(5):661-7, and International application WO99/10478 (common lymphoid progenitor); and is reviewed by Kondo et al. (2003) Annu Rev Immunol. 21:759-806, each of which is herein specifically incorporated by reference.

CD34+ cells harbor virtually all in vitro clonogenic potential; however, the CD34+ population is heterogeneous. Only a small fraction (1-10%) of CD34+ cells that do not express mature lineage markers (Lin$^-$, including the markers CD3, CD4, CD8, CD19, CD20, CD56, CD11b, CD14, and CD15) have multilineage (lymphoid and myeloid) developmental potential. The majority of CD34+ cells (90-99%) coexpress the CD38 antigen, and this subset contains most of the lineage-restricted progenitors.

In the myeloid lineage are three cell populations, termed CMPs, GMPs, and MEPs. These cells are CD34$^+$ CD38$^+$, they are negative for multiple mature lineage markers including early lymphoid markers such as CD7, CD10, and IL-7R, and they are further distinguished by the markers CD45RA, an isoform of CD45 that can negatively regulate at least some classes of cytokine receptor signaling, and IL-3R. These characteristics are CD45RA$^-$ IL-3Rα$^{lo}$ (CMPs), CD45RA$^+$IL-3Rα$^{lo}$ (GMPs), and CD45RA$^-$IL-3Rα$^-$ (MEPs). CD45RA$^-$ IL-3Rα$^{lo}$ cells give rise to GMPs and MEPs and at least one third generate both GM and MegE colonies on a single-cell level.

In both human and mouse cells, all three of the myeloid lineage progenitors stain negatively for the markers Thy-1 (CD90), IL-7Rα (CD127); and with a panel of lineage markers, which lineage markers may include CD2; CD3; CD4; CD7; CD8; CD10; CD11 b; CD14; CD19; CD20; CD56; and glycophorin A (GPA) in humans and CD2; CD3; CD4; CD8; CD19; IgM; Ter110; Gr-1 in mice. With the exception of the mouse MEP subset, all of the progenitor cells are CD34 positive. In the mouse all of the progenitor subsets may be further characterized as Sca-1 negative, (Ly-6E and Ly-6A), and c-kit high. In the human, all three of the subsets are CD38$^+$.

In the mouse, the CD34 and Fcγ receptor (FcγR) are useful in distinguishing these subsets. The CMP is characterized as FcγR$^{lo}$CD34$^+$ population; the GMP is FcγR$^{hi}$ CD34$^+$; and the MEP subset is FcγR$^{lo}$CD34$^-$.

In the presence of steel factor (SLF), flt-3 ligand (FL), interleukin (IL)-3, IL-11, GM-CSF, thrombopoietin (Tpo) and erythropoietin (Epo), the CMP cells give rise to various types of myeloerythroid colonies, including CFU-GEMMeg, burst-forming unit-erythroid (BFU-E), CFU-megakaryocytes (CFU-Meg), CFU-granulocyte/macrophage (CFU-GM), CFU-granulocyte (CFU-G) and CFU-macrophage (CFU-M). The GMP subset generates CFU-M, CFU-G, or CFU-GM colonies containing macrophages and/or granulocytes in response to the above growth factors. In contrast, the MEP subset gives rise to CFU-Meg, BFU-E, or CFU-MEP colonies containing only megakaryocytes and/or erythrocytes in response to IL-3, GM-CSF, Tpo and Epo, but do not form colonies in the absence of Tpo and Epo. All three myeloid progenitor populations do not require "early-acting cytokines" such as SLF, FL and IL-11 to initiate colony formation.

All of these progenitors are capable of rapid differentiation activity in vivo. CMP cells give rise to Gr-1+/Mac-1+ myelomonocytic cells and megakaryocytic colonies, as well as TER119+ erythroid cells in spleen and bone marrow. The GMP progenitor population gives rise to Gr-1+/Mac-1+ cells; and the MEP progenitor population to megakaryocytes and erythroid cells.

Other progenitor subsets that may find use in leukemia staging include the common lymphoid progenitor, e.g. in analysis of lymphocytic leukemias. Common lymphoid progenitors, CLP, express low levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit. The CLP cells express high levels of the IL-7 receptor alpha chain (CDw127). Antibodies that bind to human or to mouse CDw127 are known in the art. Alternatively, the cells are identified by binding of the ligand to the receptor, IL-7.

Murine CLPs express low levels of Sca-1 (Ly-6E and Ly-6A, see van de Rijn (1989) *Proc Natl Acad Sci* 86:4634-4638). Human CLPs express low levels of CD34. Antibodies specific for human CD34 are commercially available and well known in the art. See, for example, Chen et al. (1997) *Immu-*

*nol Rev* 157:41-51. Human CLP cells are also characterized as CD38 positive and CD10 positive.

The CLP subset also has the phenotype of lacking expression of lineage specific markers, exemplified by B220, CD4, CD8, CD3, Gr-1 and Mac-1. The CLP cells are characterized as lacking expression of Thy-1, a marker that is characteristic of hematopoietic stem cells. The phenotype of the CLP may be further characterized as Mel-14$^-$, CD43$^{lo}$, HSA$^{lo}$, CD45$^+$ and common cytokine receptor y chain positive.

The analysis of megakaryocyte progenitors may also be of interest. The MKP cells are positive for CD34 expression, and tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. The MKP cells express CD41, also referred to as the glycoprotein IIb/IIIa integrin, which is the platelet receptor for fibrinogen and several other extracellular matrix molecules, for which antibodies are commercially available, for example from BD Biosciences, Pharmingen, San Diego, Calif., catalog number 340929, 555466. The MKP cells are positive for expression of CD117, which recognizes the receptor tyrosine kinase c-Kit. Antibodies are commercially available, for example from BD Biosciences, Pharmingen, San Diego, Calif., Cat. No. 340529. MKP cells are also lineage negative, and negative for expression of Thy-1 (CD90).

Myeloproliferative Disorders, Leukemias, and Myelodysplactic Syndrome

Chronic leukemias include chronic myelogenous leukemia (CML); chronic myelomonocytic leukemia, and chronic lymphocytic leukemia. Clonal myeloproliferation of CML is caused by malignant transformation of an early hematopoietic cell, and is characterized clinically by striking overproduction of granulocytes, primarily in the bone marrow but also in extramedullary sites. The neoplastic clone may include RBC, megakaryocyte, monocyte, and even some T and B cells. Normal stem cells are retained and can emerge after drug suppression of the CML clone. In most patients, the CML clone progresses to an accelerated phase and final blast crisis.

In the symptomatic patient, the WBC count is usually about $2 \times 10^5$/μl but may reach $10^6$/μl. The platelet count is normal or moderately increased. On blood smears, all stages of granulocyte differentiation are seen. The absolute eosinophil and basophil concentrations can be strikingly increased, but the absolute lymphocyte and monocyte concentrations may be normal. The bone marrow is hypercellular on aspirate and biopsy. The Philadelphia chromosome can be demonstrated in almost all patients by chromosomal analysis.

During the accelerated phase of disease progression, anemia and thrombocytopenia develop. Basophils may increase, and granulocyte maturation may be defective. The proportion of immature cells and the neutrophil alkaline phosphatase score may increase. In the bone marrow, myelofibrosis may develop and sideroblasts may be seen on microscopy. Further evolution may lead to a blast crisis with myeloblasts, lymphoblasts, and megakaryocytoblasts.

Imatinib mesylate is the drug of choice for most cases, although patients may also be treated with interferon, hydroxyurea, cytarabine, and other myelosuppressive drugs such as 6-mercaptopurine, 6-thioguanine, melphalan, and cyclophosphamide. In the absence of stem cell transplantation, for most cases the Ph-positive clone persists in the marrow.

Chronic Myelomonocytic Leukemias (CMML) include two types: an adult type referred to as CMML and a form of childhood leukemia called Juvenile Myelomonocytic Leukemia (JMML) or Juvenile Chronic Myelogenous Leukemia (JCML). CMML leukemias have features that are characteristic of myelogenous leukemia. CMML is more rapidly progressive than "typical" chronic myelogenous leukemia and less rapidly progressive than acute myelomonocytic leukemia.

JMML occurs most often in infants and children under four years of age. The blood cell and bone marrow findings are similar in some respects to adult chronic myelomonocytic leukemia. Both disorders are cancers that originate in a marrow cell. Infants with JMML fail to thrive. Low hemoglobin (anemia), low platelets, and moderate increases in white cell count are common. The blood invariably has an increased concentration of monocytes and immature granulocytes (myelocytes), hence the term "myelomonocytic" leukemia. The Ph chromosome, characteristic of typical chronic myelogenous leukemia is not present. JMML has been resistant to chemotherapy. The median survival of patients with the juvenile form of the disease is usually less than two years.

Adult type chronic myelomonocytic leukemia is part of the spectrum of myelogenous leukemias that may have findings that simulate typical chronic myelogenous leukemia (CML) such as anemia, high white cell count and enlargement of the spleen. However, the cells do not contain the Ph chromosome, or BCR-ABL oncogene, that characterizes chronic myelogenous leukemia. Most patients with chronic myelomonocytic leukemia (CMML) are over 50 years of age. Blood cell counts may be variable with CMML. The white blood cell count may be slightly decreased, normal, or moderately elevated. Immature granulocytes (myelocytes) may be present in the blood. Blood myeloblasts may be absent or, when present, are in low proportions. In some cases, a translocation of chromosomes 5 and 12, occurs, resulting in the PDGFR-b-TEL gene translocation.

Chronic leukocytic leukemia (CLL) is the clonal expansion of mature-appearing lymphocytes involving lymph nodes and other lymphoid tissues with progressive infiltration of bone marrow and presence in the peripheral blood. Most cases are diagnosed in elderly patients. Lymphocyte accumulation probably begins in the bone marrow and spreads to lymph nodes and other lymphoid tissues. Usually in late disease, abnormal hematopoiesis results in anemia, neutropenia, thrombocytopenia, and decreased immunoglobulin production. Traditional delineation of CLL has been of the most common subtype (B-cell form), which represents almost all cases, and a rare T cell type. In addition, other chronic leukemic patterns have been categorized under CLL: prolymphocytic leukemia, leukemic phase of cutaneous T-cell lymphoma, hairy cell leukemia, and lymphoma leukemia.

The hallmark of CLL is sustained, absolute lymphocytosis and increased lymphocytes in the bone marrow. CBC and bone marrow aspiration confirm diagnosis. Although CLL is progressive, some patients may be asymptomatic for years; therapy is not indicated until active progression or symptoms occur. Specific therapy includes chemotherapy, corticosteroids, and radiotherapy. Alkylating drugs, especially chlorambucil, alone or with corticosteroids, fludarabine, IFN-γ, deoxycoformycin, and 2-chlorodeoxyadenosine are also of use.

Acute leukemias are rapidly progressing leukemia characterized by replacement of normal bone marrow by blast cells of a clone arising from malignant transformation of a hematopoietic stem cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas).

The presenting symptoms are usually nonspecific (e.g., fatigue, fever, malaise, weight loss) and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

ALL is the most common malignancy in children, with a peak incidence from ages 3 to 5 yr. It also occurs in adolescents and has a second, lower peak in adults. Typical treatment emphasizes early introduction of an intensive multidrug regimen, which may include prednisone, vincristine, anthracycline or asparaginase. Other drugs and combinations are cytarabine and etoposide, and cyclophosphamide. Relapse usually occurs in the bone marrow but may also occur in the CNS or testes, alone or concurrent with bone marrow. Although second remissions can be induced in many children, subsequent remissions tend to be brief.

The incidence of AML increases with age; it is the more common acute leukemia in adults. AML may be associated with chemotherapy or irradiation (secondary AML). Remission induction rates are lower than with ALL, and long-term disease-free survival reportedly occurs in only 20 to 40% of patients. Treatment differs most from ALL in that AML responds to fewer drugs. The basic induction regimen includes cytarabine; along with daunorubicin or idarubicin. Some regimens include 6-thioguanine, etoposide, vincristine, and prednisone.

Polycythemia vera (PV) is an idiopathic chronic myeloproliferative disorder characterized by an increase in Hb concentration and RBC mass (erythrocytosis). PV occurs in about 2.3/100,000 people per year; more often in males (about 1.4:1). The mean age at diagnosis is 60 yr (range, 15 to 90 yr; rarely in childhood); 5% of patients are <40 yr at onset. The bone marrow sometimes appears normal but usually is hypercellular; hyperplasia involves all marrow elements and replaces marrow fat. There is increased production and turnover of RBCs, neutrophils, and platelets. Increased megakaryocytes may be present in clumps. Marrow iron is absent in >90% of patients, even when phlebotomy has not been performed.

Studies of women with PV who are heterozygous at the X-chromosome-linked locus for G6PD have shown that RBCs, neutrophils, and platelets have the same G6PD isoenzyme, supporting a clonal origin of this disorder at a pluripotent stem cell level. The cause of this proliferation is unknown.

Eventually, about 25% of patients have reduced RBC survival and fail to adequately increase erythropoiesis; anemia and myelofibrosis develop. Extramedullary hemopoiesis occurs in the spleen, liver, and other sites with the potential for blood cell formation.

Without treatment, 50% of symptomatic patients die within 18 mo of diagnosis. (For information about support for the patient and family, see Ch. 294.) With treatment, median survival is 7 to 15 yr. Thrombosis is the most common cause of death, followed by complications of myeloid metaplasia, hemorrhage, and development of leukemia.

The incidence of transformation into an acute leukemia is greater in patients treated with radioactive phosphate (32P) or alkylating agents than in those treated with phlebotomy alone. PV that transforms into acute leukemia is more resistant to induction chemotherapy than de novo leukemia.

Because PV is the only form of erythrocytosis for which myelosuppressive therapy may be indicated, accurate diagnosis is critical. Therapy must be individualized according to age, sex, medical status, clinical manifestations, and hematologic findings.

Essential Thrombocythemia (ET) is a disease characterized by an increased platelet count, megakaryocytic hyperplasia, and a hemorrhagic or thrombotic tendency. ET is a clonal abnormality of a multipotent hematopoietic stem cell. It usually occurs between ages 50 and 70 yr and affects men and women equally. Markedly elevated platelet counts result from increased platelet production. Platelet survival is usually normal, although it may be decreased owing to splenic sequestration. In older patients with degenerative vascular disease, an increased platelet count may lead to serious bleeding or thrombosis.

ET should be differentiated from other myeloproliferative disorders associated with an elevated platelet count. Diagnostic requirements for primary thrombocythemia include a normal RBC mass (increased in polycythemia vera), absence of the Philadelphia chromosome (found in chronic myelogenous leukemia), and absence of teardrop-shaped RBCs or significant increase in bone marrow fibrosis (seen in idiopathic myelofibrosis). The platelet count can be >1×106/µL, although counts as low as 500,000/µL may occur.

In the peripheral smear, platelet aggregates, giant platelets, and megakaryocyte fragments may be found. The bone marrow shows megakaryocytic hyperplasia, with an abundance of platelets being released. Marrow iron is usually present.

Indications for therapy for primary thrombocythemia are unclear, although in patients with platelet counts >1×106/µL and in those with hemorrhage or thrombotic complications, most authorities believe that definitive therapy is indicated.

Agnogenic Myeloid Metaplasia with myelofibrosis (AMM) is a chronic, usually idiopathic disease characterized by bone marrow fibrosis, splenomegaly, and leukoerythroblastic anemia with teardrop-shaped RBCs. The cause of AMM is unknown. It may complicate chronic myelogenous leukemia and occurs in 15 to 30% of patients with polycythemia vera if they survive long enough. Syndromes similar to idiopathic myelofibrosis have been associated with various tumors and infections and after exposure to certain toxins. Malignant or acute myelofibrosis, an unusual variant, has a more rapidly progressive downhill course this may actually be a true megakaryocytic leukemia.

The peak incidence of idiopathic myelofibrosis is between 50 and 70 yr. The median survival is 10 yr from estimated onset. Studies based on G6PD isoenzymes and chromosome abnormalities suggest that clonal proliferation of an abnormal myeloid stem cell occurs. Because marrow fibroblasts do not arise from the same hematopoietic clone, as confirmed by analysis of marrow fibroblasts after marrow transplantation, it is believed that a major feature of the disease, the myelofibrosis, is a complicating, reactive feature of a primary disease process.

Changes in the blood cells are variable. Anemia is usual and generally increases over time. RBCs are normochromic-normocytic with mild poikilocytosis, reticulocytosis, and polychromatophilia. Nucleated RBCs may be found in peripheral blood. In advanced cases, RBCs are severely misshapen and teardrop-shaped; their appearance is sufficiently abnormal to suggest the diagnosis.

WBC counts are usually increased but are highly variable. Neutrophil immaturity occurs in most patients, and the presence of myeloblasts is not necessarily indicative of conversion to acute leukemia. Platelet counts initially may be high, normal, or decreased; however, thrombocytopenia tends to supervene as the disease progresses.

Bone marrow aspiration is usually dry. A bone marrow biopsy is required to show fibrosis. Because fibrosis may not be uniformly distributed, biopsy should be repeated at a different site in patients with suspected idiopathic myelofibrosis if the first biopsy is nondiagnostic.

Because there is no therapy to reverse or control the underlying pathologic process, although interferon is being evaluated treatment of AMM is directed at management of complications. Androgens, splenectomy, chemotherapy (hydroxyurea), and radiotherapy have sometimes been used for palliation. For patients with low erythropoietin levels relative to the degree of anemia, erythropoietin sc may minimize the need for RBC transfusion. Transfusion of packed RBCs for severe anemia is an important aspect of therapy. For younger patients with advanced disease, allogeneic marrow transplantation should be considered.

Myelodysplastic syndrome (MDS) is a group of syndromes (preleukemia, refractory anemias, Ph-negative chronic myelocytic leukemia, chronic myelomonocytic leukemia, agnogenic myeloid metaplasia) commonly seen in older patients. Exposure to carcinogens may by implicated. MDS is characterized by clonal proliferation of hematopoietic cells, including erythroid, myeloid, and megakaryocytic forms. The bone marrow is normal or hypercellular, and ineffective hematopoiesis causes variable cytopenias, the most frequent being anemia. The disordered cell production is also associated with morphologic cellular abnormalities in marrow and blood. Extramedullary hematopoiesis may occur, leading to hepatomegaly and splenomegaly. Myelofibrosis is occasionally present at diagnosis or may develop during the course of MDS. The MDS clone is unstable and tends to progress to AML.

Anemia is the most common clinical feature, associated usually with macrocytosis and anisocytosis. Some degree of thrombocytopenia is usual; on blood smear, the platelets vary in size, and some appear hypogranular. The WBC count may be normal, increased, or decreased. Neutrophil cytoplasmic granularity is abnormal, with anisocytosis and variable numbers of granules. Eosinophils also may have abnormal granularity. A monocytosis is characteristic of the chronic myelomonocytic leukemia subgroup, and immature myeloid cells may occur in the less well differentiated subgroups. The prognosis is highly dependent on classification and on any associated disease. Response of MDS to AML chemotherapy is similar to that of AML, after age and karyotype are considered.

Differential Progenitor Cell Analysis

Clinical samples for use in the methods of the invention may be obtained from a variety of sources, particularly blood, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cell staining will use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

The comparison of a differential progenitor analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Analysis of normal and leukemic hematopoietic samples allows determination of the stage of a leukemia. During progression of leukemic disease, which as used herein may refer to pre-leukemic and leukemic conditions, there is a significant expansion of $CD34^+$ cells in the blood, and a dramatic decline in these populations after successful drug treatment. Even more striking is the identification herein of shifting distributions of cells within this compartment, where the differential distribution of cells in the HSC, CMP, MEP and GMP populations is highly correlated with the stage of disease in myelogenous leukemias. The distribution of cells in lymphocytic leukemias may also be diagnostic, particularly the distribution between HSC and lymphoid committed progenitors.

In further characterizing the hematopoietic stem and progenitor cells from patients with blood disorders, gene expression analyses can be employed. In general, gene expression profiles obtained from the patients are compared to normal samples and/or those from a subject with a known blood disorder. Gene expression analysis of hematopoietic stem and progenitor cells can be accomplished using a variety of techniques known in the art. Examples of methods of gene expression analyses known in the art include semi-quantitative and quantitative RT-PCR, DNA arrays or microarrays, protein arrays and proteomics, differential display, comparative genomic hybridization, and mass spectrometry methods.

For patients with adult CMML, the percentage of hematopoietic stem cells in blood samples are increased relative to normal samples. CMML cells are also characterized by changes in gene expression as compared to normal bone marrow cells. For example, CMML cells have increased expression of the myeloid transcription factor PU.1 beginning at the level of HSC and a coincident decrease in transcription of the erythroid transcription factor GATA-1. The HSC compartment is also increased in drug resistant CML, relative to both normal and other stages of the disease. CML accelerated phase is also distinguished from chronic or blast crisis phase CML by consistently aberrant expression of CD90 by CD34+CD38+ cells. CML blast crisis is typified by an expansion of both $CD34^+CD38^-$ and $CD34^+CD38^+$ progenitors.

Cell surface expression of Flk2/Flt3, a tyrosine kinase that is frequently mutated or overexpressed in poor prognosis AML, is elevated in $CD34^+CD38^-CD90^+$ and $CD90^-Lin-$ cells in advanced phases of CML.

Differential analysis of committed myeloid progenitor profiles ($CD34^+CD38^+Lin^-$) provides a means of distinguishing chronic, accelerated and blast crisis. Chronic phase is typified by an expansion of megakaryocyte erythroid progenitors (MEP). Accelerated phase is characterized by increased common myeloid progenitors (CMP). Myeloid blast crisis is characterized by a greater proportion of granulocyte macrophage progenitors (GMP) compared with normal bone marrow.

In imatinib responsive patients the proportion of individual myeloid progenitors reverted to normal, whereas imatinib resistant bone marrow or peripheral blood demonstrated an expansion of both HSCs and GMPs more typical of blast crisis.

CD47, also known as integrin associated protein, is a ubiquitously expressed cell surface glycoprotein that interacts with a number of integrins, thereby, modulating leukocyte adhesion, migration, cell motility and platelet activation. CD47 is also the ligand for the macrophage inhibitory receptor signal regulatory protein (SIRPα) and thus, impairs macrophage-mediated phagocytosis.

Progression of human myeloproliferative disorders (MPDs) to AML is characterized by an expansion of the GMP pool compared with normal bone marrow and an increase in CD47 expression in HSC and committed progenitors to the myeloid lineage. Thus, in accordance with the present invention, increased CD47 expression serves as a useful diagnostic marker for progression to AML and provides a novel therapeutic target.

Progenitor analysis of MPD samples revealed that atypical (BCR-ABL-negative) chronic myelogenous leukemia (aCML), blast crisis CML, and AML are characterized by increased granulocyte-macrophage progenitors (GMP) while PV and ET samples are characterized by decreased GMP, relative to a normal control. PV samples are also characterized by a distinctive interleukin-3 receptor-a high population that distinguished it from all other MPDs. Compared to normal samples, PV samples are characterized as having skewed development toward the erythroid lineage at the HSC level. In contrast, chronic myelomonocytic leukemia (CMML), aCML and AML HSC are characterized as being skewed towards myeloid colonies in vitro. The JAK2 V617F mutation is detectable within HSC and their progeny in the majority of MPDs, but not in all. The aberrant erythroid potential of PV HSC in vitro is potently inhibited with a JAK2 inhibitor.

Systems and Kits

Systems and kits of the invention may contain a staining reagents that are sufficient to differentially identify the $CD34^+$ stem and progenitor subsets described herein. A marker combination of interest may include CD34 and CD38, CD45RA and IL-3Rα. In other embodiments, CD90 may be included. CD47 and Flk2 are found to be indicative of CMML. Lineage panels may be included to distinguish progenitor cells from lineage committed cells. The staining reagents are preferably antibodies, and may be detectably labeled. Systems and kits of the invention may also include tubes, buffers, etc., and instructions for use. In addition, reagents for the analysis of gene expression can also be provided. These reagent can be for analyzing global gene expression patterns (e.g., for use in microarray analyses) or may be specific for a specific gene or gene product (e.g., transcription factors like Pu.1, GATA-1, GATA-2, c-jun, CEBP-α, etc.). Control reagents may also be provided.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

EXPERIMENTAL EXAMPLE 1

Profiling of Human Myeloproliferative Disorders

Materials and Methods

Samples

MPD peripheral blood (n=20) and bone marrow samples (n=9) were donated by patients with PV (n=17), ET (n=7), MF or post-polycythemic myeloid metaplasia with myelofibrosis (PPMM) (n=5), aCM-UMPD unclassified (MPD-U) (n=2), CML (n=7), and CMML (n=11). In addition, AML samples were provided by patients with de novo AML (n=4) and those whose disease had evolved from CMML (n=9). Normal bone marrow or cord blood (n=14) and peripheral blood samples (n=2) were provided by healthy volunteers. Normal, MPD and AML samples were obtained with informed consent according to Stanford University IRB approved protocols. Normal bone marrow and cord blood samples were also purchased from All Cells™.

Flow-Cytometric Analysis and Cell Sorting

Mononuclear fractions were extracted from peripheral blood or bone marrow following Ficoll density centrifugation according to standard methods. Samples were analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 (RPA-2.10), CD11b (ICRF44), CD20 (2H7), CD56 (B159), GPA (GA-R2) from Becton Dickinson—PharMingen, San Diego, CD3 (S4.1), CD4 (S3.5), CD7 (CD7-6B7), CD8 (3B5), CD10 (5-1B4), CD14 (TUK4), CD19 (SJ25-C1) from Caltag, South San Francisco, Calif. and APC-conjugated anti-CD34 (HPCA-2; Becton Dickinson-PharMingen), biotinylated anti-CD38 (HIT2; Caltag) in addition to PE-conjugated anti-IL-3Rα (9F5; Becton Dickinson-ParMingen) and FITC-conjugated anti-CD45RA (MEM56; Caltag) followed by staining with Streptavidin-Alexa 594 to visualize CD38-biotin stained cells and resuspension in propidium iodide to exclude dead cells. Unstained samples and isotype controls were included to assess background fluorescence. Following staining, cells were analyzed and sorted using a modified FACS Vantage (Becton Dickinson Immunocytometry Systems, Mountain View, Calif.) equipped with a 599 nm dye laser and a 488 nm argon laser. Double sorted hematopoietic stem cells(HSC) were identified as CD34+CD38−CD90+ and lineage negative. Common myeloid progenitors (CMP) were identified based on CD34+CD38+IL-3Rα+CD45RA−lin− staining and their progeny including granulocyte/macrophage progenitors (GMP) were CD34+CD38+IL-3Rα+CD45RA+lin− while megakaryocyte/erythrocyte progenitors (MEP) were identified based on CD34+CD38+IL-3Rα−CD45RA−lin− staining (Manz, Jamieson)

Hematopoietic Progenitor Assays

Normal and MPD HSC, common myeloid progenitors (CMP), granulocyte-macrophage progenitors (GMP), and megakaryocyte-erythroid progenitors (MEP) were sorted with the aid of a FACS Vantage directly onto 35 mm plates containing complete methylcellulose (GF+H4435, StemCell Technologies. Inc., Vancouver, Canada) according to manufacturer specifications, with or without 50 μM of the JAK2 inhibitor AG490 (Tyrphostin B42, Calbiochem, San Diego, Calif.). Colonies were incubated in a 37° C. 7% CO2 humidified incubator and scored on day 10-14 as colony forming unit mix (CFU-Mix), burst-forming unit erythroid/colony forming unit-erythroid (BFUE/CFU-E), CFU-granulocyte (CFU-G), CFU-macrophage (CFU-M), CFU megakaryocyte (CFU-MK) or CFU-granulocyte-macrophage (CFU-GM).2 Phase contrast photomicrographs of colonies were obtained on day 14 with a Zeiss axiovert microscope at 100x magnification with the aid of SPOT software.

JAK2 Mutation Screening

Mononuclear Cells

Sequencing for the JAK2 V617F mutation was performed on peripheral blood or bone marrow mononuclear cells derived from patients with MPDs, as well as normal bone marrow and cord blood. Red blood cells were lysed, and DNA was extracted with the QiaAmp DNA Blood Mini kit according to the manufacturer's directions (Qiagen, Valencia, Calif.) and then stored at −80° C. until amplification-based testing. Extracted DNA was prepared for JAK2 mutation analysis by LightCycler methodology.

Hematopoietic Stem Cell and Progenitor Targeted JAK2 Mutation Analysis

Targeted JAK2 V617F sequencing analysis was performed on cDNA derived from FACS-sorted HSC, CMP, GMP and MEP from normal peripheral blood, bone marrow or cord blood versus MPD peripheral blood or bone marrow. In some experiments, methylcellulose containing colonies (whole plate) derived from individual progenitor populations was resuspended in 1 ml of trizol, RNA extracted, cDNA made and sequenced for the JAK2 V61 7F mutation.

Clonal JAK2 Mutation Analysis

To further investigate whether JAK2 V617F occurred as a clonal mutation, sequencing analysis of JAK2 was performed on individual colonies derived from HSC, CMP, GMP and MEP populations with or without in vitro inhibition of JAK2 with AG490. Individual colonies were plucked and resuspended in 200 microliters of RLT buffer supplemented with β-mercaptoethanol (Qiagen RNeasy™) and frozen immediately at −80° C. Samples were thawed and RNA extracted followed by cDNA preparation and PCR amplification with JAK2 specific primers.

Mutation Scanning and DNA Sequencing

Mutation analysis of the JAK2 cDNA PCR product was conducted using fluorescent denaturing high performance liquid chromatography (DHPLC) technology and SURVEYOR mismatch cleavage analysis both with the WAVE-HS System (Transgenomic, Gaithersberg, Md.). Aliquots of PCR product (3-15 ul) were scanned for mutations by DHPLC, confirmed by Surveyor mismatch cleavage, and identified with bidirectional sequence analysis on an ABI 3100 sequencer using BigDye V3.1 terminator chemistry (Applied Biosystems, Inc., Foster City, Calif.). For semi-quantitative determination of mutant and normal allele frequencies, relative peak areas of DHPLC elution profiles and Surveyor mismatch cleavage products were determined after normalization and comparison to reference controls using the WAVE Navigator software.

Statistical Analysis

Standard deviation, standard error of the mean and mean percentages of HSC and progenitors were measured using FloJo and Excel software. Two-tailed Student's t-Test (Excel software) was used to analyze statistical differences in the proportion of different progenitor populations between MPD subtypes and normal controls.

Light-Cycler-based Melting Curve Analysis of JAK2 V617F

LightCycler™ methodology employs a forward and reverse primer pair to amplify a 233 base pair product spanning the JAK2 mutation site. Two probe sets with fluorophores (FITC and Cy5) lie in close proximity to each other and hybridize to the amplified products. A shorter probe spanning and specific to the mutation (V617F) site has a shorter melting temperature (Tm). While lying in close proximity, fluorescence from one probe excites the other by a process of FRET (Fluorescence Resonance Energy Transfer). Primers and Probes were designed using GenBank sequence NM_004972 and optimized using LightCycler Probe Design Software v1.0 (Idaho Technology, Salt Lake City, Utah). In the presence of the V617F mutation, the shorter probe dissociates early as the temperature is increased resulting in loss of fluorescence at a lower Tm (55° C.±2.5), which is detected by fluorescence detectors. If the mutation site is absent, both probes dissociate at 59.5° C., resulting in a melting peak at a higher Tm. Analysis was performed in the Lightcycler instrument (Roche, Indianapolis, Ind.). For the PCR reaction 50 ng of genomic DNA was amplified with the LC FastStart DNA master Hyb probe kit (Roche). Each 10 microL reaction contained 1× Lightcycler-FastStart Reaction Mix Hybridization Probes, 1.5 mM MgCl2 , 500 nM each forward and reverse primers, 200 nM each hybridization probe. The amplification conditions consisted of one denaturation/activation cycle of 10 minutes at 95° C., 40 cycles of three-temperature amplification. Each cycle was 95° C. for 5 sec, 55° C. for 5 sec, and 72° C. for 10 sec with a single fluorescent acquisition step at the 55° C. hold. This was followed by a melting curve analysis of 95° C. for 10 sec, 45° C. for 60 sec and a slow ramp. (1° C./sec) to 75° C. with continuous fluorescent acquisition.

```
JAK2-        5'-ACAACAGTCAAACAACAATTC-3'
forward      [SEQ ID NO:1]

JAK2-        5'-ACACCTAGCTGTGATCC-3'
reverse      [SEQ ID NO:2]

JAK2-wild    5'-LCred640-CGTCTCCACAGACACATACTC-
type         C3blocker-3' [SEQ ID NO:3]

JAK2-an2     5'-AAAGGCATTAGAAAGCCTGTAGTTTTACTTACTCT-
             Fluo-3' [SEQ ID NO:4]
```

Hematopoietic Stem Cell and Progenitor Targeted JAK Mutation Analysis

Sample preparation and RNA Extraction

Total RNA was extracted from 190 samples including snap-frozen cells and colonies using either the RNeasy® Mini Protocol (Qiagen, Germantown, Md.) or TRIZOL® reagent (Invitrogen, Carlsbad, Calif.) according to the instructions of the manufacturers. All samples were quantified using the NanoDrop® ND-1000 Spectrophotometer (Wilmington, Del.) and re-suspended at working concentrations of 50 ng/ul in RNAase free water.

Reverse Transcription and Polymerase Chain Reaction (RT-PCR)

RT-PCR amplification of 500 ng of purified RNA was performed with the SuperScript One-Step RT-PCR System with Platinum® Taq (Invitrogen, Carlsbad, Calif.) in individual tubes for each RNA sample, with 1.0 ul of the One-Step RT-PCR Platinum Taq enzyme mixture included in a 2× reaction buffer containing, 0.4 mM of each dNTP, 2.4 mM MgSO4 and 0.2 uM of the sense and anti-sense gene specific JAK2 primers in a final reaction volume of 25 ul. Reverse transcription and PCR cycling steps were carried out in a MJ Research Dyad thermocycler. The conditions for RT-PCR included cDNA synthesis at 50° C. for 30 min followed by a 2 min denaturing step at 94° C.; and PCR for 35 cycles of denaturation (94° C., 15 sec), annealing (58° C., 30sec), and extension (68° C., 60 sec) followed by a final extension step of 1 cycle at 68° C. for 5 min. JAK2 primers used in both the RT-PCR and PCR amplifications were:

Primary JAK2 primers

```
(forward)    5'-TAAAGGCGTACGAAGAGAAGTAGGAGACT-3'
             [SEQ ID NO:5]

(reverse)    5'-GGCCCATGCCAACTGTTTAGC-3'
             [SEQ ID NO:6]
```

These primers amplify a 301 bp cDNA product that contains JAK2 exon 14, which harbors codon V617. In the event that this One-Step RT-PCR amplification didn't yield enough analyzable PCR product, a nested PCR amplification was performed using the product of the One-Step RT-PCR as template in a separate reaction using:

Secondary JAK2 primers

```
(forward)    5'-ACGGTCAACTGCATGAAACA-3'
             [SEQ ID NO:7]

(reverse)    5'-GTTGCTAAACAGTTGGCATGG-3'
             [SEQ ID NO:8]
```

These primers amplify a 269 bp cDNA product. Nested PCR was performed using 50 ng of the One-Step RT-PCR product as template in a separate 50 ul reaction which consisted of final concentrations of 1.25U of HotMaster Taq DNA Polymerase (Eppendorf), HotMaster Taq Buffer with 2.5 mM Mg2+ (25 mM Tris-HCL pH 8.0, 35 mM KCL, 0.1 mM EDTA, 1 mM DDT, 50% glycerol, 0.5% Tween20, 0.5%IGEPAL CA-630 and stabilizers), 2 mM of each dNTP, 0.2 uM of each nested sense and anti-sense primer. These primers also served as nested sequencing primers.

Results

Phenotypic Progenitor Profiles Distinguish Different Forms of MPD

Figure 1B:
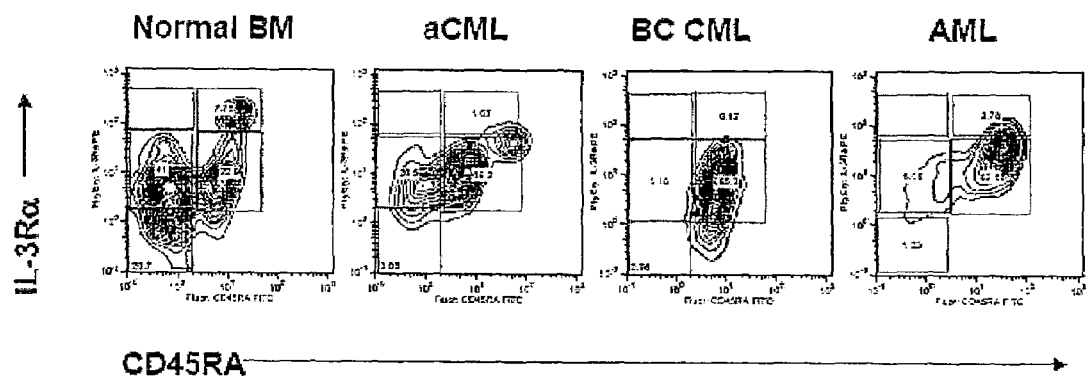
FIG. 1B. Representative FACS plots show increased GMP in MPD with skewed myeloid differentiation potential including MPD-unclassifiable (MPD-U), proliferative phase CMML, CML blast crisis, and AML compared with normal bone marrow.
Figure 1C:
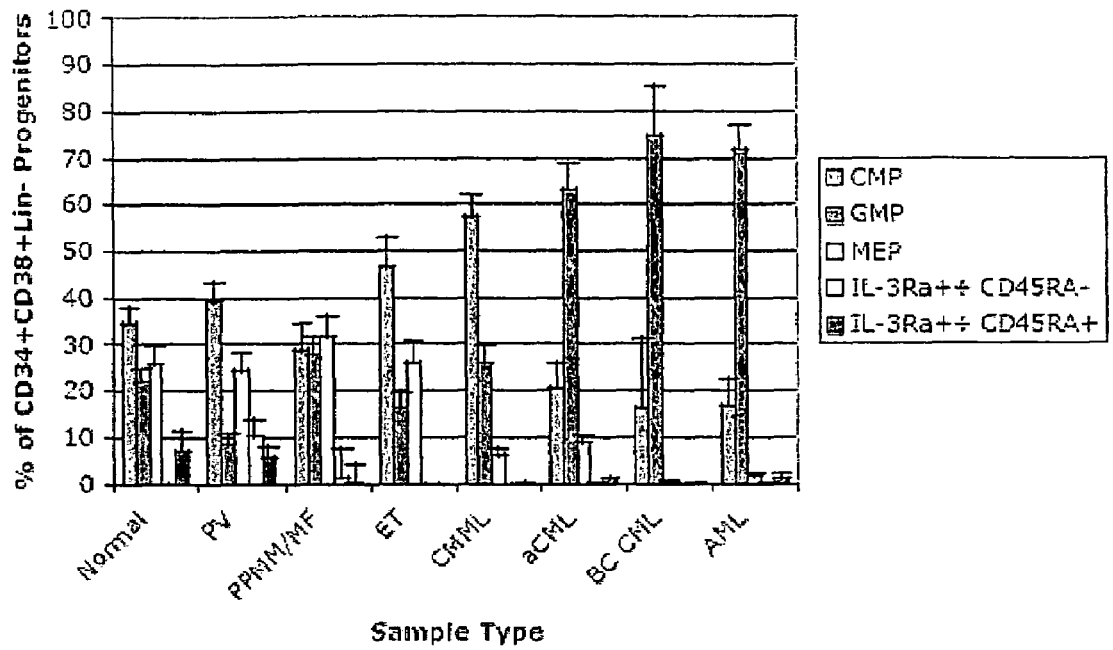
FIG. 1C. The percentage (+/– SEM) of common myeloid progenitors (CMP), granulocyte-macrophage progenitors (GMP), megakaryocyte-erythroid progenitors (MEP), IL-3Ra++CD45RA– and IL-3Ra++CD45RA+ cells within the CD34+CD38+Linpopulation was analyzed via FACS in normal bone marrow or cord blood (normal; n=7), or polycythemia vera (PV; n=11), MF/post-polycythemic myelofibrosis with myeloid metaplasia (MF/PPMM; n=3), essential thrombocythemia (ET; n=6), chronic myelomonocytic leukemia (CMML; n=12), atypical CML/MPD-unclassifiable (aCML/MPD-U; n=2), blast crisis CML (BC CML; n=2), acute myelogenous leukemia (AML; n=4) bone marrow or peripheral blood. Student's t-Test analysis revealed a statistically significant decrease in GMP in PV ($p=0.001$) and ET ($p=0.03$), while aCML ($p=0.0002$), BC CML ($p=0.0001$) and AML ($p=0.000005$) showed a statistically significant increase in GMP. Also, there was a significant decrease in MEP in CMML ($p=0.00006$), BC CML ($p=0.02$) and AML ($p=0.002$) samples. Finally, PV samples had a characteristic increase ($p=0.04$) in IL-3Ra++CD45RA− cells compared with normal samples.

Flow cytometric analysis of HSC and progenitor populations derived from 53 MPD and 13 AML patient peripheral blood and bone marrow samples (Table 1) revealed distinctive progenitor profiles for different MPD subtypes. Compared to normal marrow or cord blood, we observed skewed erythroid or megakaryocytic differentiation potential in PV, PPMM, and ET (FIG. 1A) versus primarily myeloid differentiation potential in atypical CMUMPD-Unclassifiable (aCMLJMPD-U) blast crisis CML (BC CML), and AML (FIG. 1B). There was a statistically significant expansion of granulocyte-macrophage progenitors (GMP) in aCMUMPD-U, BC CML, and AML, accompanied by a corresponding decrement in the percentage of megakaryocyte-erythroid progenitors (MEP) in these diseases, as well as CMML (FIG. 1C). Conversely, ET (n=6) and PV (n=11) had a significant decrease in GMP compared with normal bone marrow or cord blood (n=7) (FIG. 1C). Furthermore, PV samples were typified by an increase in a previously unidentified CD34+CD38+ IL-3Rα++CD45RA' lineage negative population.

Altered Hematopoietic Stem Cell Fates in MPDs

Figure 2A:
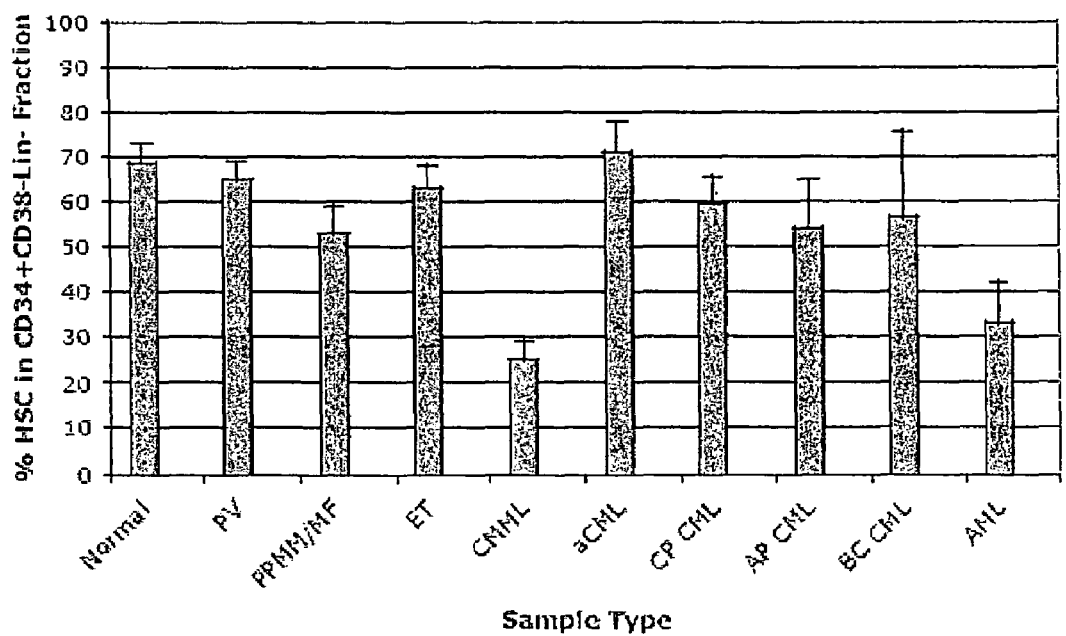
FIG. 2A. Hematopoietic Stem Cells do not increase in MPD compared with normal bone marrow. The proportion of hematopoietic stem cells (HSC) does not increase in myeloproliferative disorders (MPD) compared with normal bone marrow. Blue bars represent the percentage (+/− standard error of the mean) of HSC (CD90+ cells) within the CD34+ CD38−Lin− fraction. Results were obtained via FACS analysis of normal bone marrow or cord blood samples (n=21) compared with polycythemia vera (PV; n=13), myelofibrosis/post-polycythemic myelofibrosis with myeloid metaplasia (PPMM/MF; n=4), essential thrombocythemia (ET; n=7), chronic myelomonocytic leukemia (CMML; n=7), atypical chronic myelogenous leukemia/MPD-unclassifiable (aCML/MPD-U; n=2), chronic phase CML (CP CML; n=6), accelerated phase CML (AP CML; n=4), blast crisis CML (BC CML; n=2), and acute myelogenous leukemia (AML; n=4). Of note, Student's t-Test statistical analysis revealed that both CMML ($p<0.001$) and AML ($p=0.002$) had a significantly lower percentage of HSC compared with normal samples.
Figure 2B:
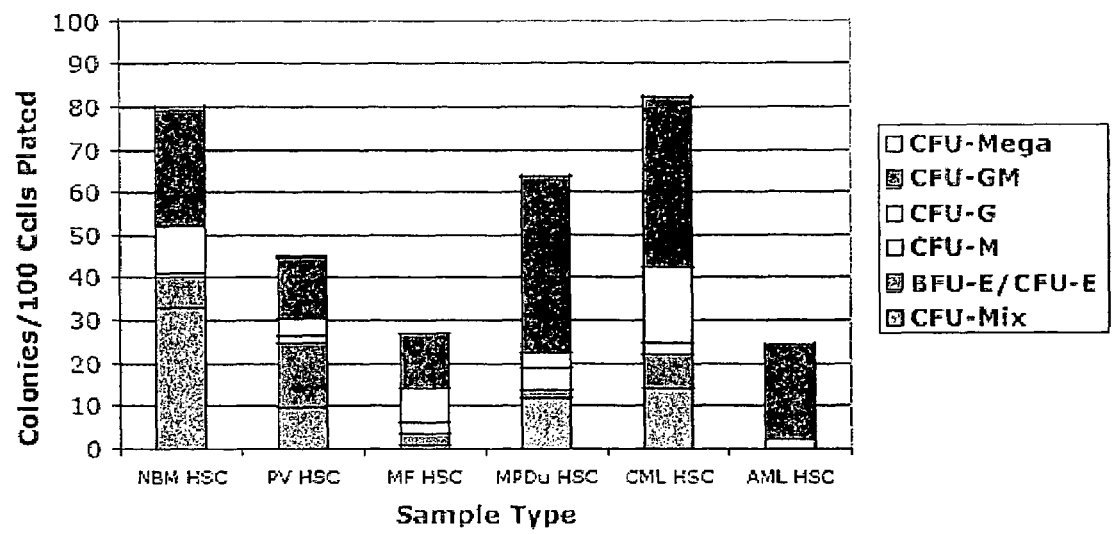
FIG. 2B. Functional analysis of differentiation potential of normal, MPD and leukemic HSC in vitro. Hematopoietic stem cells (HSC) derived from normal bone marrow or cord blood (NBM; n=8), or polycythemia vera (PV; n=11), myelofibrosis/post-polycythemic myelofibrosis with myeloid metaplasia (MF/PPMM; n=3), myeloproliferative disease unspecified/atypical CML (MPDu/aCML;n=4), chronic myelogenous leukemia (CML; n=3), acute myelogenous leukemia (AML; n=2). Bone marrow or peripheral blood were FACS sorted onto methylcellulose supplemented with cytokines.
Figure 2C:
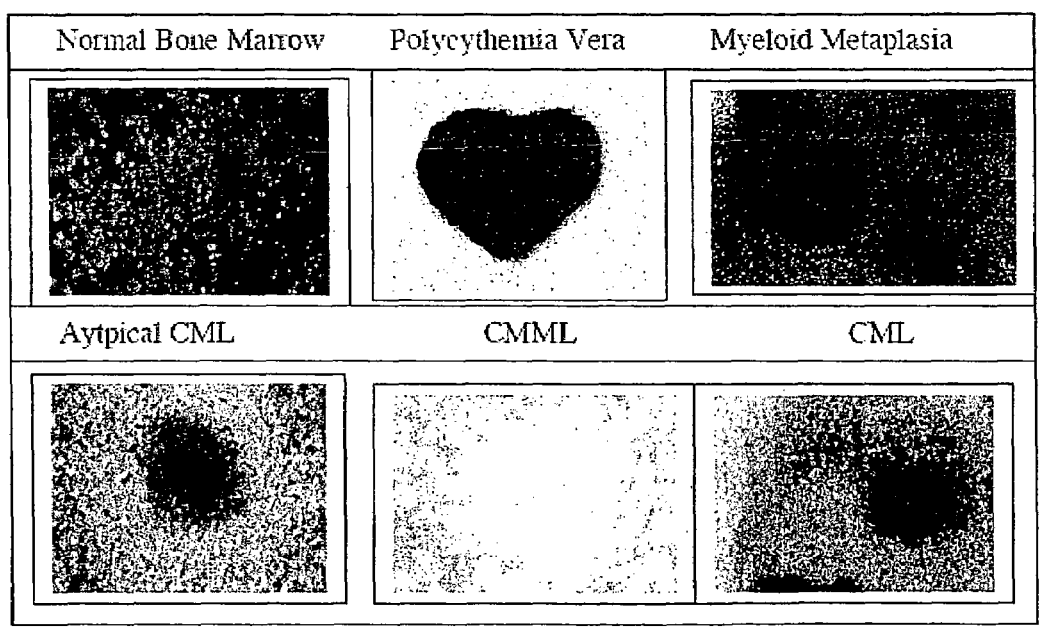
FIG. 2C. Altered in vitro differentiation potential of MPD HSC. Photomicrographs (10× objective) of colonies derived from hematopoietic stem cells (HSC). Highly purified HSC derived from normal bone marrow or cord blood (NBM; n=8), or polycythemia vera (PV; n=11), myelofibrosis/post-polycythemic myelofibrosis with myeloid metaplasia (MF/PPMM; n=3), atypical CML/myeloproliferative disorder unclassifiable (aCML/MPD-U; n=4), chronic myelogenous leukemia (CML; n=3), chronic myelomonocytic leukemia (CMML; n=14), or chronic myelogenous leukemia (CML; n=3). Bone marrow or peripheral blood were FACS sorted onto methylcellulose supplemented with cytokines.

FACS analysis of the proportion of HSC (CD34+CD38−CD90+lineage−) in PV (n=13), PPMM/MF (n=4), ET (n=7), CMML (n=7), aCML/MPD-U (n=2), chronic phase (CP) CML (n=6), accelerated phase (AP) CML (n=4), BC CML (n=2) and AML (n=4) bone marrow or peripheral blood revealed that there was no expansion in the HSC compartment compared with normal bone marrow or cord blood (n=21) suggesting that there was no in vivo proliferative advantage for HSC in MPDs (FIG. 2A). However, hematopoietic progenitor assays revealed an alteration in cell fate at the stem cell level in MPDs compared with normal bone marrow or cord blood. Depending on the MPD subtype, there were both quantitative (FIG. 2B) and qualitative (FIG. 2C) differences in the colony types derived from HSC compared with normal samples. While PV HSC gave rise to a preponderance of large, abnormally shaped erythroid colonies, MPDs with skewed myeloid differentiation potential, such as aCML/MPD-U, CMML, CML and AML, gave rise to primarily myeloid colonies including CFU-GM, CFU-G and CFU-M (FIG. 2C).

TABLE 1

Patient Characteristics

| Patient No. | Age/Sex | Clinical Diagnosis | Disease-Specific Treatment at Time of Sample Evaluation | Sample Source | JAK2 V617F Mutation Status (PB) |
|---|---|---|---|---|---|
| 1 | 43/M | PV | Phlebotomy, hydroxyurea | PB | + |
| 2 | 59/F | PV | Phlebotomy | PB | + |
| 3 | 62/M | PV | Phlebotomy, hydroxyurea | PB/BM | + |
| 4 | 68/F | PV | Hydroxyurea | PB | + |
| 5 | 47/F | PV | Phlebotomy | PB | + |
| 6 | 63/M | PV | Phlebotomy | PB | ND |
| 7 | 68/F | PV | Phlebotomy | PB | + |
| 8 | 30/M | PV | Phlebotomy | PB | − |
| 9 | 65/F | PV | Phlebotomy | PB | + |
| 10 | 48/M | PV | Phlebotomy | PB | + |
| 11 | 61/F | PV | Phlebotomy, hydroxyurea | PB | + |
| 12 | 46/M | PV | Phlebotomy, hydroxyurea | PB | + |
| 13 | 68/M | PV | Phlebotomy | PB | + |
| 14 | 80/M | PV | Phlebotomy, hydroxyurea | PB | + |
| 15 | 70/F | PV | Phlebotomy, hydroxyurea | PB | + |
| 16 | 39/M | PV | Phlebotomy | PB | − |
| 17 | 51/M | PV vs. 2° polycythemia | Phlebotomy | PB | − |
| 18 | 71/M | PPMM | Busulfan, prednisone | PB | ND |
| 19 | 76/F | PPMM | Busulfan | PB | + |
| 20 | 57/M | PPMM | Hydroxyurea | PB | + |
| 21 | 50/F | ET | Hydroxyurea | PB | ND |
| 22 | 66/M | ET | None | PB | − |
| 23 | 58/F | ET | Hydroxyurea | PB | + |
| 24 | 74/F | ET | Aspirin only | PB | + |
| 25 | 40/F | ET | Aspirin only | PB | − |
| 26 | 38/F | ET | Anagrelide, aspirin | PB | − |
| 27 | 48/M | ET | Clopidogrel, aspirin | PB | Indeterminate |
| 28 | 71/M | AMM | Erythropoietin | PB | + |
| 29 | 56/F | AMM | None | PB | − |

TABLE 1-continued

Patient Characteristics

| Patient No. | Age/Sex | Clinical Diagnosis | Disease-Specific Treatment at Time of Sample Evaluation | Sample Source | JAK2 V617F Mutation Status (PB) |
|---|---|---|---|---|---|
| 30 | 70/M | MDS/MPD, U | RBC transfusion | PB | + |
| 31 | 75/M | Atypical CML | None | PB | ND |
| 32 | 56/F | CP CML | Imatinib + tipifarnib | BM | − |
| 33 | 53/M | CP CML | Imatinib | PB | ND |
| 34 | 71/F | CP CML | None | PB | ND |
| 35 | 60/M | CP CML | Imatinib | PB | ND |
| 36a | 51/F | CP CML | Tipifarnib | PB | ND |
| b | | L-BC CML | Tipifarnib | PB | − |
| 37 | 38/F | M-BC CML | Imatinib | BM | ND |
| 38 | 62/M | AP CML | Imatinib, hydroxyurea | BM | ND |
| 39 | 58/M | AP CML | Dasatinib | BM | ND |
| 40 | 44/F | AP CML | Imatinib, hydroxyurea, | BM | ND |
| 41 | 50/F | F-P+CEL | Imatinib | BM | ND |
| 42 | 59/M | CMML-1 | None | PB | ND |
| 43 | 67/M | CMML-1 | None | BM | ND |
| 44 | 53/F | CMML-1 | RBC transfusion only | BM | ND |
| 45 | 31/M | CMML-1 | Hydroxyurea, erythropoietin | BM | ND |
| 46 | 76/M | CMML-1, ITP | Prednisone | BM | ND |
| 47 | 77/M | CMML-2 | None | BM | ND |
| 48 | 73/M | CMML-1 | None | PB | ND |
| 49 | 49/M | CMML-1 | Hydroxyurea | BM | ND |
| 50 | 69/M | M4 AML from CMML | None | BM | ND |
| 51a | 58/F | CMML-1 | Tipifarnib | BM | ND |
| b | | M5 AML from CMML | Hydroxyurea | BM | |
| 52a | 67/M | CMML-1 | Darbepoetin | BM | ND |
| b | | M5 AML from CMML | Darbepoetin | BM | |
| 53a | 57/M | CMML-1 | Tipifarnib | BM | ND |
| b | | M6 AML from CMML | Tipifarnib | BM | |
| 54 | 68/M | AML | Cytarabine | BM | ND |
| 55 | 80/M | M1 AML from CMML | Tipifarnib | BM | ND |
| 56 | 71/M | M4 AML from CMML | Hydroxyurea | BM | ND |
| 57 | 58/M | M4 AML from CMML | Hydroxyurea | BM | ND |
| 58 | 75/F | M4 AML from CMML | None | BM | ND |
| 59 | 80/F | M5 AML from CMML | Hydroxyurea | PB | ND |
| 60 | 58/F | Relapsed M2 AML | None | PB | ND |
| 61 | 51/F | M5 AML | None | PB | ND |
| 62 | 52/M | AML NOS | None | PB | ND |

PB = peripheral blood;
PPMM = post-polycythemic myeloid metaplasia with myelofibrosis;
PV = polycythemia vera;
MDS/MPD, U = myelodysplastic syndrome/myeloproliferative disorder, unclassifiable;
RBC = red blood cell;
CML = chronic myelogenous leukemia;
ET = essential thrombocythemia;
AMM = agnogenic myeloid metaplasia with myelofibrosis;
CML = chronic myelogenous leukemia;
CP = chronic phase;
AP = accelerated phase;
L-BC = lymphoid blast crisis;
M-BC = myeloid blast crisis;
Ph+ = Philadelphia chromosome-positive;
F-P+CEL = FIP1L1-PDGFRA-positive chronic eosinophilic leukemia;
CMML = chronic myelomonocytic leukemia;
ITP; idiopathic thrombocytopenic purpura;
AML = acute myelogenous leukemia;
NOS = not otherwise specified;
ND = not determined The JAK2 V617F Mutation is Present in MPD HSC Of the 27 MPD samples tested, including PV, ET, myeloid metaplasia/myelofibrosis, UMPD/atypical CML and CML, 19 had evidence of the JAK2 V617F mutation in the mononuclear cell fraction derived from peripheral blood or bone marrow (Table 1). In patients identified as having the JAK2 V617F mutation in the mononuclear cell fraction, a more targeted molecular analysis demonstrated that the JAK2 V617F mutation was also detectable in highly purified HSC from 4 of 6 PV, 3 of 3 ET, 2 of 2 aCML/MPD-U, and 0 of 4 normal bone marrow or cord blood samples tested (Table 2A). In patients with HSC involvement by JAK2 V617F, the mutation could also be detected in the CMP and/or GMP fractions in 4 of 5 patients analyzed, and in the MEP fraction in 3 of 3 patients. In addition, the JAK2 V6i7F mutation was found in the unique IL-3 receptor α-high fraction of a PV sample, but was absent in all normal (n=5) HSC and progenitor populations tested. The mutant allele frequency was similar between HSC and more differentiated progeny, including the CMP, GMP, and MEP fractions (Table 2A).

TABLE 2A

Detection of the JAK2 V617F Mutation in Hematopoietic Stem Cells (HSC) and Myeloid Progenitors, and from Individual Colonies Derived from Sorted Progenitors

| | | | Analysis of JAK2 V617F in Sorted Progenitors | | | | | Clonal Analysis of JAK2 V617F from Individual Colonies Derived from Sorted Progenitors | | | |
|---|---|---|---|---|---|---|---|---|---|---|---|
| Pt. # | Diagnosis | PB JAK2 7617F | HSC | # positive/# samples tested [Mutant Allele Frequency] CMP | GMP | MEP | IL-3R++ | Derivative Progenitor | +/− AG490 50 uM | # positive colonies/# colonies screened | [Mutant Allele Frequency] |
| 2 | PV | + | 1/3 [0.1] | 0/1 | | 1/1 [0.5] | | HSC | − | 5/17 | [<0.1, 0.1, 0.2, 0.2, 1.0] |
| | | | | | | | | HSC | + | 3/10 | [0.5, 0.9, 1.0] |
| | | | | | | | | CMP | − | 0/13 | |
| | | | | | | | | CMP | + | 2/11 | [<0.1, <0.1] |
| | | | | | | | | CMP | − | 1/1 | [1.0] |
| | | | | | | | | MEP | − | 1/1 | [0.6] |
| 9 | PV | + | 1/1 [0.75] | 1/1 [0.5] | 1/1 [0.75] | 1/1 [0.5] | | HSC | − | 3/5 | [0.4, 0.5, 0.5] |
| | | | | | | | | HSC | + | 3/4 | [<0.1, 0.5, 0.5] |
| | | | | | | | | CMP | − | 4/4 | [<0.1, 0.2, 0.4, 0.5] |
| | | | | | | | | CMP | + | 4/5 | [<0.1, 0.25, 0.6, 0.6] |
| 11 | PV | + | | | | | | HSC | − | 1/4 | [0.2] |
| | | | | | | | | HSC | + | 0/1 | |
| | | | | | | | | CMP | − | 0/3 | |
| | | | | | | | | CMP | + | 4/5 | [<0.1, 0.2, 0.4, 0.5] |
| 19 | PPMM | + | | | | | | HSC | − | 1/1 | [1.0] |
| | | | | | | | | HSC | + | 1/1 | [1.0] |
| | | | | | | | | CMP | | 0/1 | |
| 8 | PV | − | 0/1 | | | | | | | | |
| 3 | PV | + | 1/1 [1.0] | | | | | | | | |
| 13 | PPMM | ND | 1/1 [0.8] | 1/1 [0.9] | 1/1 [1.0] | 1/1 [0.9] | | | | | |
| 12 | PV | + | 1/1 [0.8] | 1/2 [0.8] | 1/1 [0.8] | ND | 1/1 [0.3] | | | | |
| 28 | MF | + | 1/1 | 70/1-HSC(CorG)MP [0.5] | | | 0/1 | | | | |

| | | | Analysis of JAK2 V617F in Sorted Progenitors | | | | | Clonal Analysis of JAK2 V617F from Individual Colonies Derived from Sorted Progenitors | | | |
|---|---|---|---|---|---|---|---|---|---|---|---|
| Normals | | PB JAK2 V617F | HSC | # positive/# samples tested Mutant Allele Frequency CMP | GMP | MEP | IL-3R++ | Derivative Progenitor | +/− AG490 50 uM | # positive colonies/# colonies screened | [Mutant Allele Frequency] |
| Normal BM-1 | | ND | | | | | | HSC | − | 0/3 | |
| | | | | | | | | HSC | + | 0/3 | |
| Normal BM-2 | | ND | | | | | | HSC | − | 0/2 | |
| | | | | | | | | HSC | + | 0/2 | |
| | | | | | | | | CMP | − | 0/3 | |
| | | | | | | | | CMP | + | 0/3 | |
| | | | | | | | | GMP | − | 0/3 | |
| | | | | | | | | MEP | − | 0/4 | |
| | | | | | | | | MEP | + | 0/4 | |
| Normal BM-3 | | ND | | | | | | HSC | − | 0/3 | |
| | | | | | | | | HSC | + | 0/2 | |
| | | | | | | | | CMP | − | 0/2 | |
| | | | | | | | | CMP | + | 0/1 | |
| Normal BM-4 | | ND | 0/1 | 0/2 | 0/2 | 0/2 | | | | | |
| Normal BM-5 | | ND | | 0/1 | 0/1 | 0/1 | | | | | |
| Normal CB | | ND | 0/1 | | 0/1 | | | | | | |

Inhibition Assays with the JAK2 Inhibitor AG490

Figure 3A:
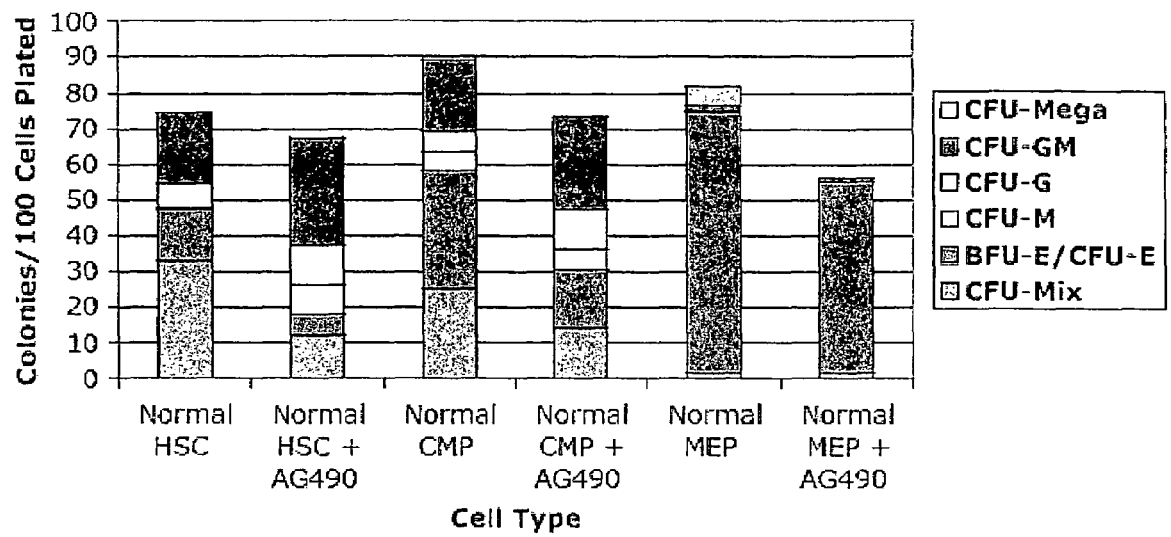
FIG. 3A. Effect of JAK2 Inhibition on normal HSC differentiation potential in vitro. Hematopoietic stem cells (HSC), common myeloid progenitors (CMP), or megakaryocyte-erythroid progenitors (MEP) derived from normal bone marrow or cord blood (n=4) were FACS sorted onto methylcellulose supplemented with or without AG490 in addition to cytokines.
Figure 3B:
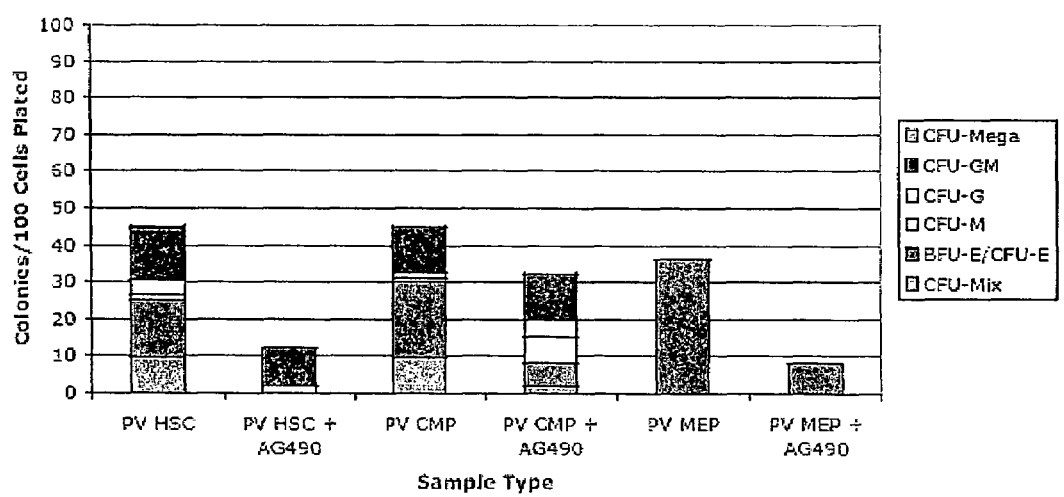
FIG. 3B. Effect of JAK2 inhibition on polycythemia vera (PV) HSC differentiation potential in vitro. Hematopoietic stem cells (HSC), common myeloid progenitors (CMP), or megakaryocyte-erythroid progenitors (MEP) derived from PV bone marrow or peripheral blood (n=5) were FACS sorted onto methylcellulose supplemented with or without AG490 in addition to cytokines.
Figure 4:
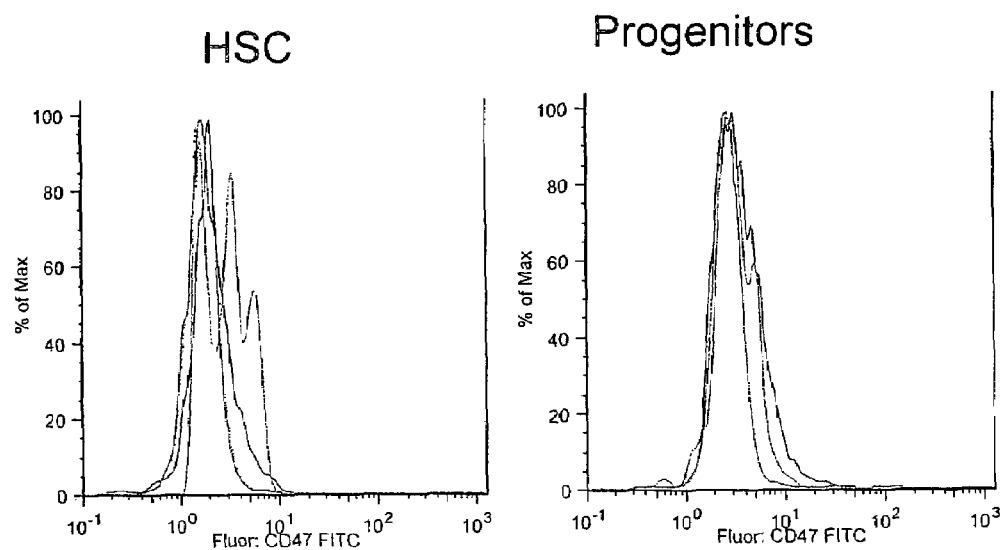
FIG. 4. FACS analysis of human HSC and progenitor CD47 expression from MDS (blue), green (CML AP) and normal bone marrow (red).
Figure 5:
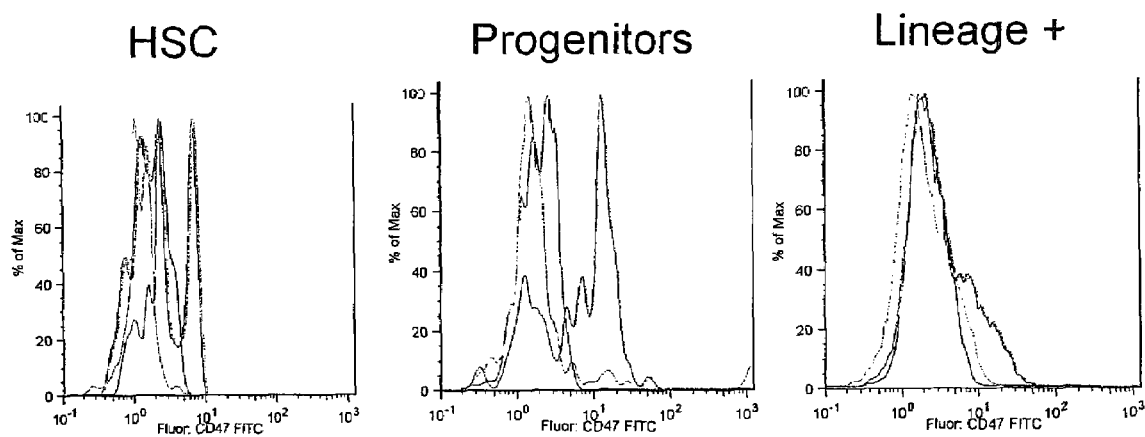
FIG. 5. ET vs. PV. FACS analysis of CD47 expression by human myeloproliferative disorders such as ET (blue) and PV (green) HSC, progenitor and lineage positive cells compared with human normal bone marrow (red).
Figure 6A:
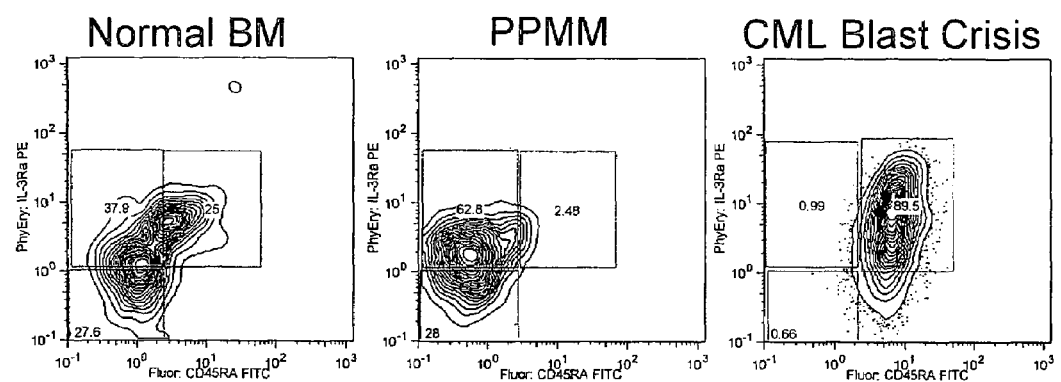
FIG. 6A. Progenitor Profiles of Normal Bone Marrow (left), PPMM and CML Blast Crisis.
Figure 6B:
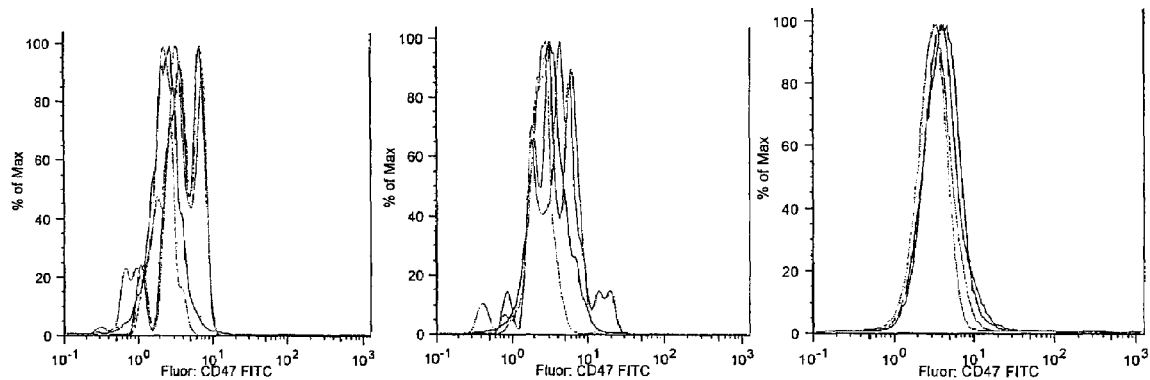
FIG. 6B. FACS analysis of human normal bone marrow (red) versus UMPD (green) versus PV (blue=ML) versus atypical CML (orange), HSC, progenitor and lineage positive cell CD47 expression.
Figure 7:
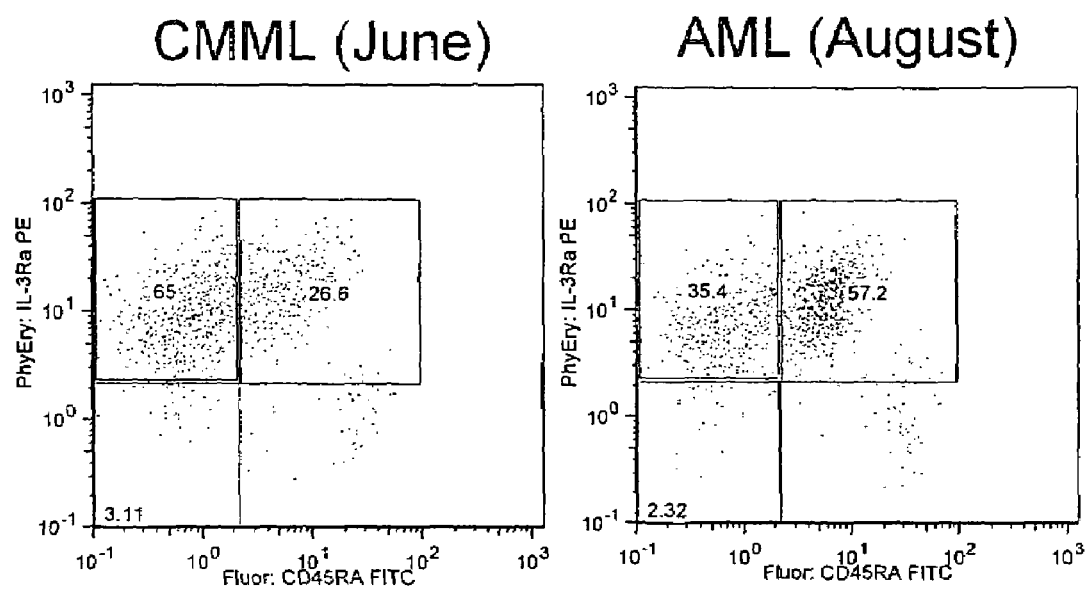
FIG. 7. Transition from increased CMP to increased GMP with CMML Progression to AML.
Figure 8:
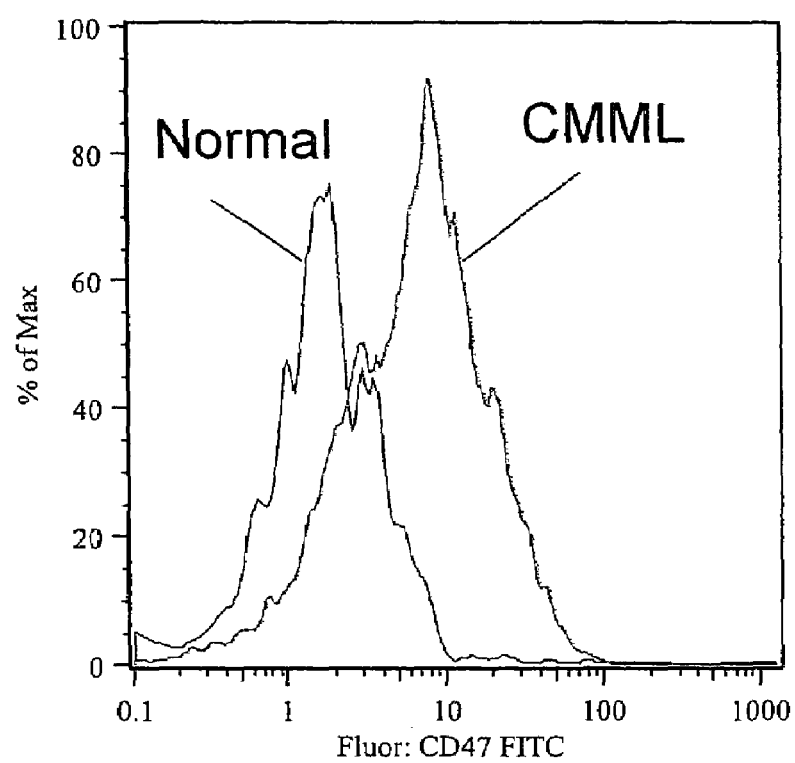
FIG. 8. Increased CD47 Expression by CMML Progenitors (blue) compared with normal bone marrow (red) with disease progression FIG. 9A. Progenitor Profiles of Normal bone marrow (left) versus AML (right).
Figure 9A:
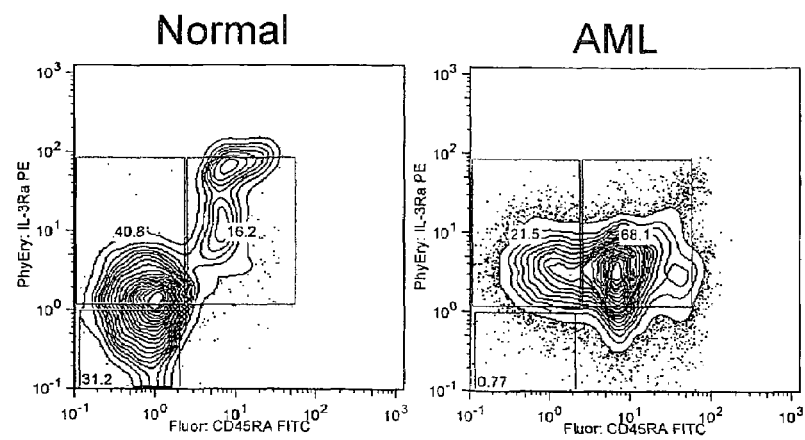
FIG. 9B. FACS analysis of human normal bone marrow (red) versus AML (blue) HSC, progenitor and lineage positive cell (blast) CD47 expression.
Figure 9B:
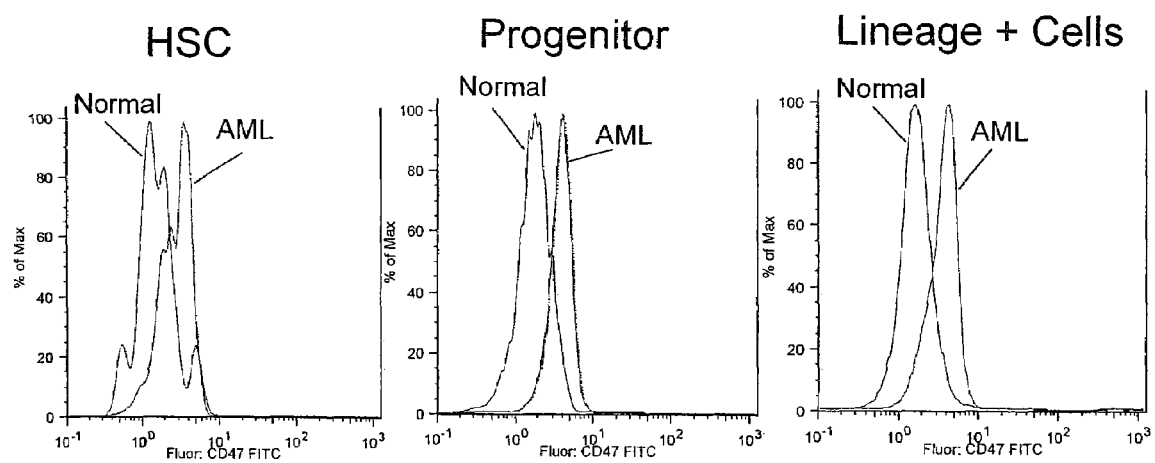

In order to ascertain whether or not JAK2 signaling played a role in the skewed differentiation potential of MPD versus normal samples, hematopoietic progenitor assays were performed in the presence or absence of AG490, a well characterized JAK2 inhibitor, at a dose (50 μM) that was previously reported to preferentially induce apoptosis in leukemic compared with normal cells (Ugo V et al, Exp Hem). When highly purified normal HSC, common myeloid progenitors (CMP) and megakaryocyte-erythroid progenitors (MEP) were exposed to AG490 in hematopoietic progenitor assays, erythroid and mixed colony formation was partially inhibited while myeloid colony formation was not detrimentally affected (FIG. 3A). In PV samples, however, there was a profound decrease in erythroid and mixed colonies derived from HSC, following exposure to AG490, while the effects were not as dramatic for CMP and MEP (FIG. 3B). Sequencing analysis of individual PV colonies derived from HSC, CMP, GMP and MEP revealed that the JAK2 V617F mutation remained in some colonies that survived treatment with AG490 indicating that some clones may be impervious to JAK2 inhibition (Table 2A).

Discussion

In this example, we combined phenotypic and functional profiling with targeted sequencing analysis of highly purified HSC and progenitors derived from a variety of MPDs in order to identify the stage of hematopoiesis at which the JAK2 V617F mutation occurs. Our data revealed six novel findings in MPDs including 1) expansion of the GMP pool in MPDs with skewed myeloid differentiation potential including aCML/MPD-U, blast crisis CML, and AML, in contrast to those with skewed erythroid or megakaryocytic differentiation potential such as PV or ET; 2) no increase in the HSC pool in MPDs, but rather 3) a quantitative and qualitative alteration in MPD differentiation potential at the HSC level; 4) HSC from a variety of MPDs harbored the JAK2 V617F mutation which 5) was transmitted in a clonal manner to more committed progenitors, and 6) the aberrant erythroid differentiation potential of PV could be inhibited at the stem cell level with a JAK2 inhibitor to a greater extent than in normal HSC.

We observed that the stem cell pool was not expanded in the peripheral blood or bone marrow of patients with JAK2 V617F-positive and JAK2 V617F-negative MPDs, while the in vitro differentiation capacity of these MPDs was profoundly altered compared to normal marrow. Without being bound by theory, these findings suggest that one of the primary defects in MPDs may be altered differentiation potential at the stem cell level rather than an initial proliferative defect. However, additional mutations are likely responsible for propagation of JAK2 V617F-positive clones, such as changes :in survival, self-renewal or replicative capacity that may hasten the progression of MPDs and evolution to acute leukemia.

We identified an IL-3 receptor a-high progenitor population which is unique to PV patients. Prior reports have shown that PV marrow BFU-E, colony-forming units granulocyte-macrophage (CFU-GM), and CFU-megakaryocyte (CFU-MK) exhibit marked hypersensitivity to recombinant IL-3. The mechanism was not found to be due to enhanced binding of recombinant IL-3 to its receptor. The growth factors to which hematopoietic progenitors are hypersensitive in MPDs (e.g. IL-3, GM-CSF, EPO, SCF, TPO, and IGF-1), all employ JAK2 for signaling, and therefore, constitutive activation of the JAK2 signaling pathway may partly explain this observation. We have used targeted JAK2 mutation screening of HSC and committed progenitors to establish the clonal hematopoietic stem cell origin of MPDs. JAK2 V617F was identified in HSC as well as CMP, GMP, MEP, and the IL-3 receptor a-high population. The mutation appears to be propagated without diminution from HSC to more committed hematopoietic progenitors.

REFERENCES FOR EXAMPLE 1

Axelrad A A, Eskinazi D, Correa P N, Amato D. Hypersensitivity of circulating progenitor cells to megakaryocyte growth and development factor (PEG-rHu MGDF) in essential thrombocythemia. Blood. 2000; 96:3310-3321.

Fialkow P J, Faguet G B, Jacobson R J, Vaidya K, Murphy S. Evidence that essential thrombocythemia is a clonal disorder with origin a multipotent stem cell. Blood. 1981;518:916-919.

Gilliland D G, Blanchard K L, Levy J, Perrin S, Bunn H F. Clonality in myeloproliferative disorders: Analysis by means of the polymerase chain reaction. Proc Natl Acad Sci U.S.A. 1991; 88:6848-6852.

Baxter J E, Scott L M, Campbell P J, et al. Acquired mutation of the tyrosine kinase JAK2 in human myeloproliferative disorders. Lancet. 2005; 365:1054-1061.

Levine R L, Wadleigh M, Cools J, et al. Activating mutation in the tyrosine kinase JAK2 in polycthemia vera, essential thrombocythemia, and myeloid metaplasia with myelofibrosis. Cancer Cell. 2005; 7:387-397.

James C, Ugo V, Le Couedic J-P, et al. A unique clonal JAK2 mutation leading to constitutive signaling causes polycythemia Vera. Nature. 2005; 434:1144-1148.

Kralovics R, Passamonti F, Buser A S, et al. A gain-of-function of JAK2 in myeloproliferative disorders. New Engl J Med. 2005; 352:1779-1790.

Kaushansky K. On the molecular origins of the chronic myeloproliferative disorders: it all makes sense. Blood 2005; 105:4187-90.

Spivak J L. The chronic myeloproliferative disorders: clonality and clinical heterogeneity. Semin Hematol 2004; 41: 1-5.

Onida F, Kantarjian H M, Smith T L, et al. Prognostic factors and scoring systems in chronic myelomonocytic leukemia: a retrospective analysis of 213 patients. Blood 2002; 99:840-9.

Manz M G, Miyamoto T, Akashi K. Weissman I L. Prospective isolation of human clonogenic common myeloid progenitors. Proc Natl Acad Sci USA. 2002;99:11872-7.

Jamieson C H, Ailles L E, Dylla S J, et al. Granulocyte-macrophage progenitors in chronic myelogenous leukemia are candidate leukemia stem cells that activate the betacatenin pathway. N Engl J Med 2004;351:657-67.

Jamieson C H M, Weissman I L, Passegue E. Chronic versus acute myelogenous leukemia: A question of self-renewal. Cancer Cell 2004;6:531-3.

Jamieson C H M, Passegue E, Weissman I L. Leukemia and leukemic stem cells. In: Gage R, ed. Stem cells in the nervous system: functional and clinical implications.

Berlin: Springer-Verlag, 2004:157-82. 19. Passegue E, Jamieson C H M, Ailles L E, and Weissman I L. Normal and leukemic hematopoiesis: are leukemias a stem cell disorder or a reacquisition of stem cell characteristics? Proc Natl Acad Sci USA 2003;100:11842-9.

Passegue E, Wagner E F, Weissman I L: JunB deficiency leads to a myeloproiiferative disorder arising from hematopoietic stem cells. Cell 2004; 119:431-43.

EXAMPLE 2

CD47 is a Marker of Myeloid Leukemias

Materials and Methods

Immunohistochemistry

Cytospins of double sorted myeloid progenitor populations (CMP, GMP), IL-3Rα high CD45 RA+ cells and CD14+c-kit+lin– cells were performed using a Shandon cytospin apparatus. Cytospins were stained with Giemsa diluted ⅕ with H20 for 10 min followed by staining with May-Grunwald for 20 minutes. Cytospins were analyzed with the aid of a Zeiss microscope.

Human Bone Marrow and Peripheral Blood Samples

Normal bone marrow samples were obtained with informed consent from 20-25 year old paid donors who were hepatitis A, B, C and HIV negative by serology (All Cells).

CMML bone marrow samples were obtained with informed consent, from previously untreated patients, at Stanford University Medical Center.

Human Bone Marrow HSC and Myeloid Progenitor Flow-Cytometric Analysis and Cell Sorting Mononuclear fractions were extracted following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 RPA-2.10; CD11b, ICRF44; CD20, 2H7; CD56, B159; GPA, GA-R2 (Becton Dickinson-PharMingen, San Diego), CD3,S4.1;CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, HPCA-2 (Becton Dickinson-PharMingen), biotinylated anti-CD38, HIT2 (Caltag) in addition to PE-conjugated anti-IL-3Rα, 9F5 (Becton Dickinson-ParMingen) and FITC-conjugated anti-CD45RA, MEM56 (Caltag) followed by staining with Streptavidin—Texas Red to visualize CD38-BIO stained cells and resuspension in propidium iodide to exclude dead cells. Unstained samples and isotype controls were included to assess background fluorescence.

Following staining, cells were analyzed and sorted using a modified FACS Vantage (Becton Dickinson Immunocytometry Systems, Mountain View, Calif.) equipped with a 599 nm dye laser and a 488 nm argon laser. Double sorted progenitor cells (HSC) were identified as CD34+ CD38+ and lineage negative. Common myeloid progenitors (CMP) were identified based on CD34+ CD38+ IL-3Rα+ CD45RA– lin– staining and their progeny including granulocyte/macrophage progenitors (GMP) were CD34+CD38+IL-3Rα+ CD45RA+ while megakaryocyte/erythrocyte progenitors (MEP) were identified based on CD34+ CD38+ IL-3Rα– CD45RA– lin– staining (Manz, PNAS 11872).

CD47 Expression by Normal Versus Myeloproliferative and AML Progenitors

Peripheral blood and bone marrow samples were obtained with informed consent from patients with myeloproliferative disorders and acute myelogenous leukemia at Stanford University Medical Center according to Stanford IRB and HIPAA regulations. Peripheral blood or bone marrow mononuclear cells ($1-5 \times 10^6$ cells) were stained with lineage cocktail as above but excluding CD7, CD11b and CD14. Subsequently, samples were stained with CD14 PE (1/25), CD47 FITC (1/25), CD38 Bio (Bio) and c-kit APC (1/25) or CD34 APC or FITC (1/50) for 45 min followed by washing and staining with Streptavidin Texas Red (1/25) for 45 min and finally resuspension in propidium iodide.

Discussion

Here we show that CD47 overexpression is characteristic of progression of human myeloproliferative disorders to AML (see FIGS. 4-9B). CD47 controls integrin function but also the ability of macrophages to phagocytose cells depending on the level of CD47 expression. Thus, aberrant CD47 expression may allow LSC to evade both innate and adaptive host immunity.

Human CD47 expression analysis was performed via FACS on human normal, pre-leukemic myeloproliferative disorder (MPD) or AML HSC, progenitors and lineage positive cells derived from marrow or peripheral blood. MPD samples (n=63) included polycythemia vera (PV; n=15), post-polycythemic myeloid metaplasia/myelofibrosls (PPMM/MF; n=5), essential thrombocythemia (ET; n=8), atypical chronic myelogenous leukemia (aCML; n=2), CML (n=7), chronic eosinophilic leukemia (CEL;n=1), chronic myelomonocytic leukemia (CMML; n=13) and acute myelogenous leukemia (AML; n=12). As we have observed with the transgenic leukemic mouse models (data not shown), progression of human myeloproliferative disorders to AML (n=12) was associated with an expansion of the GMP pool (70.6%±S.D. 2.15) compared with normal bone marrow (14.7%±S.D. 2.3). Furthermore, FACS analysis revealed that CD47 expression first increased 1.7 fold in AML compared with normal HSC and then increased to 2.2 fold greater than normal with commitment of AML progenitors to the myeloid lineage. CD47 was over-expressed by AML primitive progenitors and their progeny but not by the majority of MPD (MFI 2.3±S.D. 0.43) compared with normal bone marrow (MFI 1.9±S.D. 0.07). Thus, increased CD47 expression is a useful diagnostic marker for progression to AML and in addition may represent a novel therapeutic target.

REFERENCES FOR EXAMPLE 2

Reddy V, Iwama A, Iotzova G, Schultz M, Elsasser A, Vangala R K, Tenen D G, Hiddemann W, Behre G (2002) Granulocyte inducer C/EPBa inactivates the myeloid master regulator PU.1: possible role in lineage commitment decisions. Blood 100:483-490.

Mateo V, Brown E J, Biron G, Rubio M, Fischer A, Le Deist F, Sarfati M (2002) CD47-induced caspase-independent cell death in normal and leukemic cells: link between phosphatidylserine exposure and cytoskeleton organization. Blood 100:2882-2990.

Gao A G, Lindberg F P, Plas D, Reynolds S, Peters M G, Brown E J (1996) Integrin-associated protein is a receptor for the C-terminal domain of thrombospondin. J Biol Chem 271: 21-24.

Vernon-wislon E F, Kee W J, Willis A C, Barclay A N, Simmons D L, Brown M H (2000) CD47 is a ligand for rat macrophage membrane signal regulatory protein SIRP (OX41) and human SIRPalpha 1. Eur J Immunol 30:2130-2137.

Oldenborg P-A, Gresham H D, Lindberg F P (2001) CD47-SIRPα regulates Fcγ and complement receptor-mediated phagocytosis. J Exp Med 193:855-862.

Ogata K, Nakamura K, Yokose N, Tamura H, Tachibana M, Taniguchi O, Iwakiri R, Hayashi T, Sakamaki H, Murai Y, Tohyama K, Tomoyasu S, Nonaka Y, Mori M, Dan K, Yoshida Y (2002) Clinical significance of phenotypic features of blasts in patients with myelodysplastic syndrome. Blood 100: 3887-3896.

Oldenborg P-A, Gresham H D, Chen Y, Izui S, Lindberg F P (2002) Lethal autoimmune hemolytic anemia in CD47-deficient diabetic (NOD) mice. Blood 99:3500-3504.

Armant M, Avice M N, Hermann P et al (1999) CD47 ligation selectively downregulates human interleukin 12 production. J Exp Med 190:1175-1182.

Demeure C E, Tanaka H, Mateo V, Rubio M, Delespesse G, Sarfati M (2000) CD47 engagement inhibits cytokine production and maturation of human dendritic cells. J Immunol 164;2193-2199.

Avice M N, Rubio M, Sergerie M, Delespesse G, Sarfati M (2000) CD47 ligation selectively inhibits the development of human naïve T cells into Th1 effectors. J Immunol 165:4624-4631.

Avice M N, Rubio M, Sergerie M, Delespess G, Sarfati M (2001) Role of cd47 in the induction of human naïve T cell anergy. J Immunol 167:2459-2468.

Latour S, Tanaka H, Demeure C et al (2001) Bidirectional negative regulation of human T and dendritic cells by CD47 and its cognate receptor signal-regulator protein alpha: down-regulation of IL-12 responsiveness and inhibition of dendritic cell activation. J Immunol 167:2547-2554.

Pfeiffer A, Bottcher A, Orso E et al (2001) Lipopolysaccharide and ceramide docking to CD14 provokes ligand-specific receptor clustering in rafts. Eur J Immunol 31:3154-3164.

Manz, M G, Miyamoto T, Akashi, K, Weissman I L (2002) Prospective isolation of human clonogenic common myeloid progenitors. Proc. Natl. Acad. Sci USA 99: 11872-11877.

EXAMPLE 3

Progenitor Profiling in CMML

Materials and Methods

Isolation of Human HSC and Myeloid Progenitors

Normal bone marrow (n=14) and peripheral blood samples (n=2) as well as peripheral blood and bone marrow samples donated by patients with chronic myelomonocytic leukemia (CMML; n=13), acute myelogenous leukemia that had evolved from CMML (n=8) and de novo AML (n=$^4$) were obtained with informed consent according to Stanford University IRB approved protocols. Normal bone marrow and cord blood samples were also purchased from All Cells™.

Mononuclear fractions were extracted from peripheral blood or bone marrow following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 (RPA-2.10), CD11b (ICRF44), CD20 (2H7), CD56 (B159), GPA (GA-R2) from Becton Dickinson-PharMingen, San Diego, CD3 (S4.1), CD4 (S3.5), CD7 (CD7-6B7), CD8 (3B5), CD10 (5-1B4), CD14 (TUK4), CD19 (SJ25-C1) from Caltag, South San Francisco, Calif. and APC-conjugated anti-CD34 (HPCA-2; Becton Dickinson-PharMingen), biotinylated anti-CD38 (HIT2; Caltag) in addition to PE-conjugated anti-IL-3Rα (9F5; Becton Dickinson-ParMingen) and FITC-conjugated anti-CD45RA (MEM56; Caltag) followed by staining with Streptavidin-Alexa 594 to visualize CD38-biotin stained cells and resuspension in propidium iodide to exclude dead cells. Unstained samples and isotype controls were included to assess background fluorescence. Following staining, cells were analyzed and sorted using a modified FACS Vantage (Becton Dickinson Immunocytometry Systems, Mountain View, Calif.) equipped with a 599 nm dye laser and a 488 nm argon laser. Double FACS-sorted hematopoietic stem cells (HSC) were identified as CD34+CD38−CD90+ and lineage negative. Common myeloid progenitors (CMP) were identified based on CD34+CD38+IL-3R□+CD45RA− lin− staining and their progeny including granulocyte/macrophage progenitors (GMP) were CD34+CD38+IL-3Rα+ CD45RA+lin− while megakaryocyte/erythrocyte progenitors (MEP) were identified based on CD34+CD38+IL-3Rα−CD45RA−lin− staining.

We used FACS analysis to identify differences in HSC and progenitor profiles between normal bone marrow (n=20), dysplastic CMML (n=4), proliferative CMML (n=9) and AML that had transformed from CMML (n=8) as well as de novo AML (n=4). Hematopoietic stem cells (HSC; CD34+CD38−CD90+Lin−), CD34+CD38−Flk2+90− (MPP) cells and myeloid progenitors including common myeloid progenitors (CMP; CD34+38+IL-3Ralpha+CD45RA−Lin−), megakaryocyte-erythroid progenitors (MEP; CD34+CD38+IL-3Ralpha−CD45RA−Lin−) and granulocyte-macrophage progenitors (GMP; CD34+CD38+IL-3Ralpha+CD45RA+Lin−) were stained, analyzed and then sorted using a modified FACS Vantage as previously described (Jamieson et al. NEJM (2004) 351:6576).

Quantitative RT-PCR Analysis

Normal and CMML HSC, CMP, GMP and MEP were FACS sorted directly into 200 microliters of RLT buffer and RNA was extracted according to the RNeasy protocol. Quantitative RT-PCR was performed for CD47, PU.1, GATA-1 and c-jun using previously described methodology(Jamieson et al. NEJM (2004) 351:6576).

Hematopoietic Progenitor Assays

Normal and CMML HSC, CMP, GMP and MEP were FACS sorted directly onto 35 mm plates containing methylcellulose (Stem Cell Technologies Inc) supplemented with cytokines including SCF, Flt3 ligand, IL-3, TPO, Epo, IL-11 and IL-6. Colonies were scored on day 14 as CFU-Mix, CFU-E, CFU-G, CFU-M or CFU-GM(Jamieson et al. NEJM (2004) 351:6576).

Results

Human CMML Hematopoietic Stem Cell and Progenitor Profiling

Of the CMML patients analyzed (Table 3), FACS revealed a reduction in HSC in the CD34+CD38− fraction within CMML bone marrow (23%) compared with normal bone marrow (62%) and an increase in CD34+CD38−CD90−Flk2+ cells in CMML (48%) compared with normal bone marrow (9%).

TABLE 3

Patient Characteristics

| Patient No. | Age/Sex | Clinical Diagnosis | Treatment at Time of Sample Evaluation | Sample Source |
|---|---|---|---|---|
| 1 | 59/M | CMML-1 | None | PB |
| 2 | 67/M | CMML-1 | None | BM |
| 3 | 53/F | CMML-1 | RBC transfusion only | BM |
| 4 | 31/M | CMML-1 | Hydroxyurea, erythropoietin | BM |
| 5 | 76/M | CMML-1, ITP | Prednisone | BM |
| 6 | 77/M | CMML-2 | None | BM |
| 7 | 73/M | CMML-1 | None | PB |
| 8 | 49/M | CMML-1 | Hydroxyurea | BM |
| 9 | 69/M | M4 AML from CMML | None | BM |

TABLE 3-continued

Patient Characteristics

| Patient No. | Age/Sex | Clinical Diagnosis | Treatment at Time of Sample Evaluation | Sample Source |
|---|---|---|---|---|
| 10a | 58/F | CMML-1 | Tipifarnib | BM |
| b |  | M5 AML from CMML | Hydroxyurea | BM |
| 11a | 67/M | CMML-1 | Darbepoetin | BM |
| b |  | M5 AML from CMML | Darbepoetin | BM |
| 12a | 57/M | CMML-1 | Tipifarnib | BM |
| b |  | M6 AML from CMML | Tipifarnib | BM |
| 13 | 68/M | AML | Cytarabine | BM |
| 14 | 80/M | M1 AML from CMML | Tipifarnib | BM |
| 15 | 71/M | M4 AML from CMML | Hydroxyurea | BM |
| 16 | 58/M | M4 AML from CMML | Hydroxyurea | BM |
| 17 | 75/F | M4 AML from CMML | None | BM |
| 18 | 80/F | M5 AML from CMML | Hydroxyurea | PB |
| 19 | 58/F | Relapsed M2 AML | None | PB |
| 20 | 51/F | M5 AML | None | PB |
| 21 | 52/M | AML NOS | None | PB |

Figure 10:
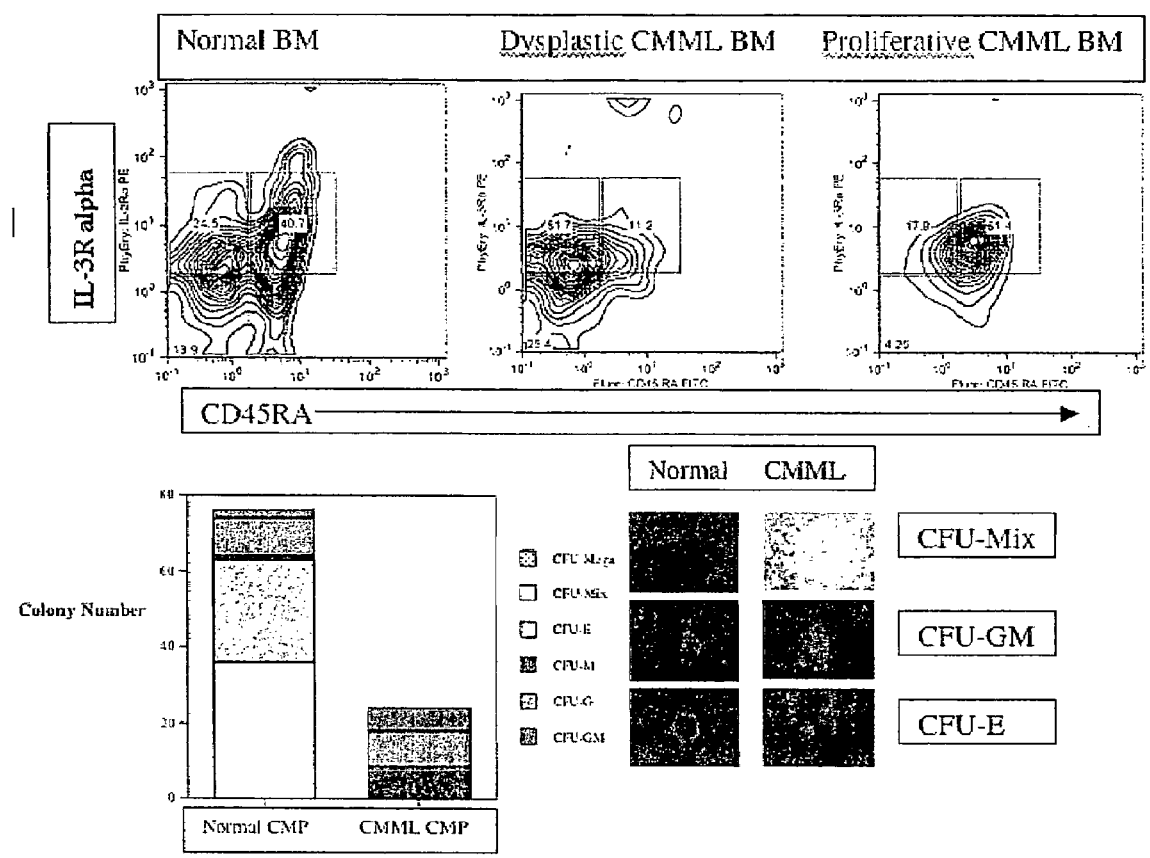
FIG. 10. Progenitor analysis revealed that CMML marrow was typified by decreased MEP (4% of progenitors) when compared with normal bone marrow (19% MEP). While dysplastic phase CMML was associated with an expansion of the CMP population, proliferative phase CMML and AML marrow was typified by an expansion of the GMP population. Myeloid progenitors from proliferative phase CMML marrow failed to give rise to erythroid colonies (CFU-E) or CFU-mix in hematopoietic progenitor assays.
Figure 11:
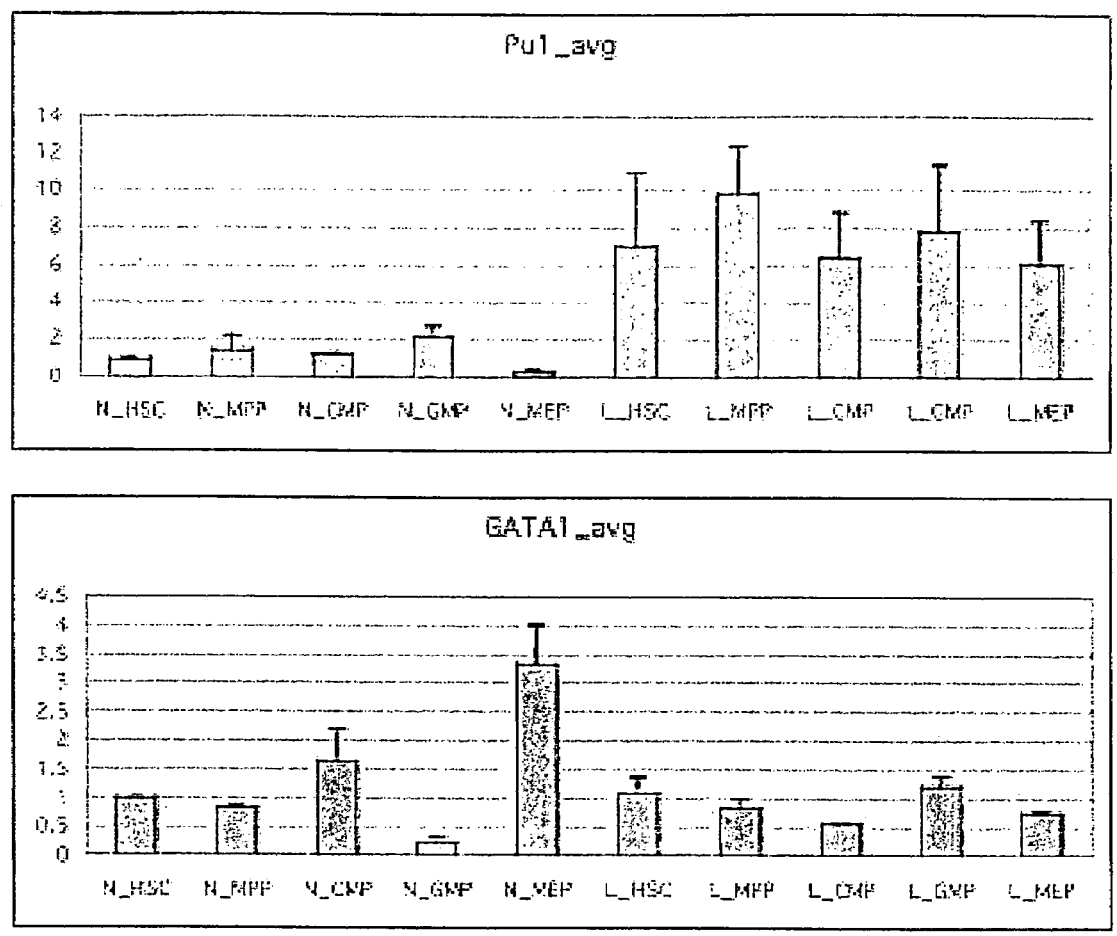
FIG. 11. Quantitative RT-PCR analysis revealed increased expression of the myeloid transcription factor, PU.1, beginning at the level of HSC and a coincident decrease in transcription of the erythroid transcription factor GATA-1 in CMML versus normal marrow (N=normal; L=leukemic, or CMML).

PB = peripheral blood;
RBC = red blood cell;
CMML = chronic myelomonocytic leukemia;
AML = acute myelogenous leukemia;
NOS = not otherwise specified;
ND = not determined Progenitor analysis revealed that CMML marrow was typified by decreased MEP (4% of progenitors) when compared with normal bone marrow (19% MEP). While dysplastic phase CMML was associated with an expansion of the CMP population, proliferative phase CMML and AML marrow was typified by an expansion of the GMP population (FIG. 10). Myeloid progenitors from proliferative phase CMML marrow failed to give rise to erythroid colonies (CFU-E) or CFU-mix in hematopoietic progenitor assays (FIG. 10). Furthermore, quantitative RT-PCR analysis revealed increased expression of the myeloid transcription factor, PU.1, beginning at the level of HSC and a coincident decrease in transcription of the erythroid transcription factor—GATA-1 in CMML versus normal marrow (FIG. 11).

As these data demonstrate, phenotypic, genetic and functional progenitor profiling provides important diagnostic and prognostic information in patients with myeloproliferative disorders.

EXAMPLE 4

Molecular Progenitor Profiling in Myeloproliferative Diseases

Methods

Gene expression profiles (GEPs) were obtained from marrow hematopoietic precursor cells (HPC)(CD34+ cells) from 30 myelodysplastic syndrome (MDS) patients: RARS 2, RA 15, RAEB 9, RAEBT 4; IPSS Low 11, Int-1 10 Int-2 5, High 4, and 6 Normal individuals. Fluorescently labeled cDNA was prepared from CD34+ cells (>90% purity), isolated by immunomagnetic column separation, after reverse transcription of high fidelity PCR-amplified poly(A) RNA (aRNA). The Cy-conjugated nucleotides for aRNA were hybridized to 40,000 gene chip microarrays obtained from the Stanford Functional Genomics Microarray Facility. aRNA from pooled normal CD34+ marrow cells was used as a Reference standard. High resolution scans were obtained to compile a dataset for each microarray, through files submitted to the Stanford Microarray Database. Dendrograms generated by unsupervised hierarchical gene clustering indicated major differences of GEP between Normal and MDS patients.

Results

Significance Analysis for Microarray (SAM) yielded 2327 genes significantly differentially expressed by MDS vs Normal: 2269 genes overexpressed, 58 underexpressed, with a false positive rate of ~10%. Prediction Analysis of Microarray (PAM) distinctly separated the MDS and Normal patients, requiring a minimum of 31 genes (which were also SAM significant). Class analysis by PAM correctly predicted 29 of the 30 to be MDS and 5 of the 6 to be Normal. Four disparate differential GEP regions in the dendrograms, comprising predominantly genes of differing functional categories and distinct from FAB/IPSS subgroups, provided signatures associated with differing MDS clinical subgroups. Nine of 10 patients with poor clinical outcomes were associated with a differing GEP signature than that which occurred in 14 of 20 patients with relatively good outcomes. Compared to the remainder of MDS patients, those with 5q-syndrome (n=5) had a differing GEP signature, with under-expression of 1018 genes, 11 of which were within the 5q31-32 CDS. Two of these genes (antioxidant protein1 and interferon regulatory factor1) have previously been proffered as candidate genes for this syndrome.

Analysis of FACS-sorted highly purified marrow HPC subsets: CD34+38+ (committed progenitors) and CD34+38− (primitive progenitors), indicated these ratios to be 4.3±2.1 (n=2) for MDS and 3.2±1.2 (n=12) for Normals. These findings indicate that the differing GEPs between the MDS and Normal CD34+ cells were not due to major differences in their proportions of CD38 cell subsets. SAM and PAM significant differential GEPs were noted between these cell subsets (also differing between MDS and Normal), indicating alteration of gene expression during differentiation. Wnt1 and β-catenin1 (genes involved in cell self-renewal) were over-expressed in both MDS CD38− and CD38+ cells compared to Normal. These data demonstrate: (1) molecular differences between MDS and Normal HPCs and within HPC subsets; (2) GEP signatures characterizing MDS patients with differing cytogenetic abnormalities (eg, 5q−) and clinical outcomes; (3) molecular criteria refining the prognostic categorization of MDS; and (4) gene expression data aiding characterization of the heterogeneous nature of this spectrum of diseases.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of staging a blood disorder comprising:
combining a hematologic sample from a patient suspected of having a blood disorder selected from the group consisting of polycythemia vera (PV); chronic myelogenous leukemia (CML); essential thrombocythemia (ET); acute myelogenous leukemia (AML); chronic myelomonocytic leukemia (CMML); post-polycythemic myeloid metaplasia (PPMM); and angiogenic myeloid metaplasia with myelofibrosis (AMM) with specific binding members that are sufficient to distinguish the distribution of hematopoietic stem and progenitor cell subsets between hematopoietic stem cells (HSC); common myeloid progenitors (CMP); megakaryocyte erythroid progenitors (MEP; granulocyte macrophage progenitors (GMP), wherein said binding members include at least one of CD47, IL-3Rα and CD45RA; and
determining the distribution of hematopoietic stem and progenitor cells between said subsets;
wherein the distribution of hematopoietic stem and progenitor cells is indicative of the phenotype of said blood disorder.

2. The method according to claim 1, wherein said determining step includes flow cytometric analysis.

3. The method according to claim 1, wherein said specific binding members are antibodies.

4. The method according to claim 3, wherein said antibodies include specificities for CD34 and CD38.

5. The method according to claim 1, further comprising antibodies specific for a lineage panel.

6. The method according to claim 1, further comprising determining a characteristic of at least one of said hematopoietic stem and progenitor cell subsets.

7. The method according to claim 6, wherein said characteristic is the expression level of at least one gene.

8. The method of claim 7, wherein said gene encodes a transcription factor.

* * * * *